US012611274B2

(12) United States Patent
Khurana et al.

(10) Patent No.: US 12,611,274 B2
(45) Date of Patent: Apr. 28, 2026

(54) ROBOTIC SURGICAL SYSTEMS AND METHODS FOR GUIDING A TOOL ALONG A PATH USING HYBRID AUTOMATED/MANUAL CONTROL

(71) Applicant: MAKO Surgical Corp., Weston, FL (US)

(72) Inventors: Rishabh Khurana, Fort Lauderdale, FL (US); Gregory Garcia, Parkland, FL (US); Huajin Qu, Fort Lauderdale, FL (US)

(73) Assignee: MAKO Surgical Corp., Weston, FL (US)

( * ) Notice: Subject to any disclaimer, the term of this patent is extended or adjusted under 35 U.S.C. 154(b) by 285 days.

(21) Appl. No.: 18/240,382

(22) Filed: Aug. 31, 2023

(65) Prior Publication Data

US 2024/0081934 A1 Mar. 14, 2024

Related U.S. Application Data

(60) Provisional application No. 63/405,083, filed on Sep. 9, 2022.

(51) Int. Cl.
*A61B 34/00* (2016.01)
*A61B 34/10* (2016.01)
(Continued)

(52) U.S. Cl.
CPC .............. *A61B 34/74* (2016.02); *A61B 34/32* (2016.02); *A61B 2034/107* (2016.02); *A61B 2034/2055* (2016.02); *A61B 2090/066* (2016.02)

(58) Field of Classification Search
CPC ... A61B 34/74; A61B 34/32; A61B 2034/107; A61B 2034/2055; A61B 2090/066;
(Continued)

(56) References Cited

U.S. PATENT DOCUMENTS 7,621,933 B2 * 11/2009 Bodduluri .............. A61B 90/36
606/187
7,621,934 B2 * 11/2009 Bodduluri ........ A61B 17/32053
606/187
(Continued)

FOREIGN PATENT DOCUMENTS

| | | |
|---|---|---|
| AU | 2019374890 A1 | 6/2021 |
| WO | 2021067438 A1 | 4/2021 |
| WO | 2022147001 A1 | 7/2022 |

OTHER PUBLICATIONS

International Search Report for Application No. PCT/US2023/031657 dated Dec. 5, 2023, 3 pages.

*Primary Examiner* — Jaime Figueroa
(74) *Attorney, Agent, or Firm* — Howard & Howard Attorneys PLLC

(57) ABSTRACT

Robotic surgical systems and methods for guiding a tool along a path using hybrid automated/manual control. A manipulator supports a surgical tool and a sensor measures forces/torques applied to the tool. A control system commands the manipulator to perform an automated advancement of the tool along a predetermined tool path in a first path direction and according to a predetermined feed rate. During the automated advancement, an input is received from the sensor in response to user applied forces/torques to the tool. The control system evaluates an effect of the sensor input on the automated advancement of the tool to determine an effective feed rate and an effective path direction for the tool with respect to the tool path. The control system determines a commanded action for the manipulator and the tool with respect to the tool path based on the effective feed rate and effective path direction.

27 Claims, 16 Drawing Sheets

(51) Int. Cl.
    *A61B 34/20*        (2016.01)
    *A61B 34/32*        (2016.01)
    *A61B 90/00*        (2016.01)

(58) Field of Classification Search
    CPC ..... A61B 17/14; A61B 17/1626; A61B 17/16;
            A61B 2017/1602; A61B 34/76; A61B
            2034/104; A61B 2034/2051; A61B
            2034/2059; A61B 34/30; A61B 2090/064
    USPC ................. 700/245–264; 318/568.11–568.25
    See application file for complete search history.

(56)             References Cited

U.S. PATENT DOCUMENTS

| | | | | |
|---|---|---|---|---|
| 8,133,247 | B2 * | 3/2012 | Bodduluri | A61B 90/36 |
| | | | | 606/187 |
| 8,317,746 | B2 | 11/2012 | Sewell et al. | |
| 8,343,096 | B2 * | 1/2013 | Kirschenman | A61M 25/0113 |
| | | | | 604/95.04 |
| 9,008,757 | B2 | 4/2015 | Wu | |
| 9,119,655 | B2 | 9/2015 | Bowling et al. | |
| 9,566,122 | B2 | 2/2017 | Bowling et al. | |
| 9,681,920 | B2 | 6/2017 | Bowling et al. | |
| 11,564,761 | B2 * | 1/2023 | Rohs | A61B 34/20 |
| 11,684,374 | B2 * | 6/2023 | Kang | A61B 34/32 |
| | | | | 606/82 |
| 12,150,713 | B2 * | 11/2024 | Saeidi | A61B 34/32 |
| 2009/0247993 | A1 * | 10/2009 | Kirschenman | A61B 34/71 |
| | | | | 606/1 |
| 2010/0330429 | A1 | 12/2010 | Yura et al. | |
| 2011/0015649 | A1 * | 1/2011 | Anvari | A61B 34/20 |
| | | | | 606/130 |
| 2014/0039517 | A1 | 2/2014 | Bowling et al. | |
| 2014/0276949 | A1 | 9/2014 | Staunton et al. | |
| 2016/0296296 | A1 * | 10/2016 | Bowling | A61B 34/30 |
| 2016/0310220 | A1 * | 10/2016 | Amiri | A61B 34/37 |
| 2018/0080841 | A1 * | 3/2018 | Cordoba | A61B 34/35 |
| 2018/0110573 | A1 | 4/2018 | Kostrzewski | |
| 2019/0314096 | A1 * | 10/2019 | Diolaiti | B25J 9/0009 |
| 2020/0237468 | A1 | 7/2020 | Johnson | |
| 2020/0281676 | A1 | 9/2020 | Rohs et al. | |
| 2020/0323540 | A1 * | 10/2020 | Kang | A61B 34/32 |
| 2020/0345433 | A1 * | 11/2020 | Peine | B25J 9/1633 |
| 2020/0405403 | A1 * | 12/2020 | Shelton, IV | A61B 17/3421 |
| 2020/0405417 | A1 * | 12/2020 | Shelton, IV | A61B 90/361 |
| 2021/0077195 | A1 | 3/2021 | Saeidi et al. | |
| 2022/0047339 | A1 * | 2/2022 | Prior | A61B 1/05 |
| 2022/0233251 | A1 | 7/2022 | Bowling et al. | |
| 2023/0320795 | A1 * | 10/2023 | Wells | A61B 34/37 |
| | | | | 606/130 |

* cited by examiner

Automated Advancement for Cut Plane Alignment

Automated Advancement (No Manual Input)

Forward Manual Input to Accelerate Automated Advancement

Forward Manual Input Release Along Forward Path Direction

Reverse Manual Input to Decelerate Forward Automated Advancement

Reverse Manual Input to Override Forward Automated Advancement

Reverse Manual Input Release Along Reverse Path Direction

Reverse Manual Input to Offset Forward Automated Advancement

Object Collision to Offset Forward Automated Advancement

ROBOTIC SURGICAL SYSTEMS AND METHODS FOR GUIDING A TOOL ALONG A PATH USING HYBRID AUTOMATED/MANUAL CONTROL

CROSS-REFERENCE TO RELATED APPLICATIONS

The subject application claims priority to, an all the benefits of, U.S. Provisional Patent App. No. 63/405,083, filed Sep. 9, 2022, the entire contents of which are hereby incorporated by reference in their entirety.

TECHNICAL FIELD

The present disclosure relates to systems and methods for guided movement of a surgical tool along a predefined path using a hybrid automated/manual control mode.

BACKGROUND

Robotic surgical systems that perform surgical procedures are well known and typically include a manipulator and a surgical tool coupled to the manipulator. Often, the surgical tool is for removing tissue at the surgical site. Robotic surgical systems have been described that can operate in different modes of operation.

One mode is a manual mode of operation whereby the robotic surgical system senses external forces/torques manually applied to the surgical tool by a user and commands positioning of the surgical tool to emulate motion expected by the user based on the applied forces/torques. Thus, in the manual mode, the robotic surgical system generally positions the surgical tool in accordance with the user's intentions and expectations. However, in the manual mode, it can be mentally and physically fatiguing for the user to direct movement of the surgical tool.

Robotic surgical systems have also been described to be operable in an automated mode in which the robotic surgical system commands the manipulator to move the surgical tool autonomously along a predefined path, without user applied forces. However, when operating in the automated mode, the user may perceive to have less control over the surgical tool.

Furthermore, techniques have been described to assist a user with guiding the surgical tool relative to the tool path. One technique involves using attractive forces or gravity wells to move the tool from a current location off the tool path to a location on the tool path. The magnitude and direction of the attractive force depends on the pose of the tool and distance of the tool to the tool path. Furthermore, the boundaries of the attractive force are virtual and may not be readily identifiable by the user when moving the tool. In turn, the attractive force can cause an unpredictable or inconsistent response which may cause some users to perceive to have less control over the tool.

Another technique involves using a guided-manual mode, as described in U.S Patent Application Publication No. US 2020/0281676 A1, entitled "Systems and Methods for Controlling Movement of a Surgical Tool Along a Predefined Path", wherein the user applies forces/torques which are utilized to determine how far to advance the tool along the tool path. In the guided-manual mode, the tool is constrained to the tool path in 2DOF normal to the tool path, but unconstrained in 1DOF tangential to the tool path. In effect, this enables the tool to freely move along the tool path based on manual force input, but the constraints guide the user by restricting the manual movement of the tool to be along the tool path. However, in the guided-manual mode, the user is still required to continually apply forces/torques to the tool in order to move the tool along the path to the final destination. Therefore, just as with the manual mode, it can be mentally and physically fatiguing for the user to direct movement of the surgical tool using the guided-manual mode.

There is a need in the art for robotic systems and methods to address these challenges by providing a mode to control movement of the surgical tool in a manner that exploits the benefits of both manual and autonomous modes for guiding the tool along a tool path.

SUMMARY

This Summary introduces a selection of concepts in a simplified form that are further described below in the Detailed Description below. This Summary is not intended to limit the scope of the claimed subject matter nor identify key features or essential features of the claimed subject matter.

According to a first aspect, a robotic surgical system is provided that comprises: a surgical tool; a manipulator configured to support the surgical tool, the manipulator comprising a plurality of links and joints; a force/torque sensor configured to measure forces/torques applied to the surgical tool by a user; and a control system configured to: obtain a predetermined tool path for the surgical tool; command the manipulator to perform an automated advancement of the surgical tool along the predetermined tool path in a first path direction and according to a predetermined feed rate; during the automated advancement of the surgical tool, receive an input from the force/torque sensor in response to forces/torques applied to the surgical tool by the user; evaluate an effect of the input from the force/torque sensor on the automated advancement of the surgical tool to determine an effective feed rate and an effective path direction for the surgical tool with respect to the predetermined tool path; and determine a commanded action for the manipulator and the surgical tool with respect to the predetermined tool path based on the effective feed rate and effective path direction.

According to a second aspect, a method is provided of operating a robotic surgical system, the robotic surgical system comprising a surgical tool, a manipulator configured to support the surgical tool, the manipulator comprising a plurality of links and joints, a force/torque sensor configured to measure forces/torques applied to the surgical tool by a user and a control system, the method comprising the control system performing the following steps: obtaining a predetermined tool path for the surgical tool; commanding the manipulator to perform an automated advancement of the surgical tool along the predetermined tool path in a first path direction and according to a predetermined feed rate; during the automated advancement of the surgical tool, receiving an input from the force/torque sensor in response to forces/torques applied to the surgical tool by the user; evaluating an effect of the input from the force/torque sensor on the automated advancement of the surgical tool for determining an effective feed rate and an effective path direction for the surgical tool with respect to the predetermined tool path; and determining a commanded action for the manipulator and the surgical tool with respect to the predetermined tool path based on the effective feed rate and effective path direction.

According to a third aspect, a robotic surgical system is provided that comprises: a surgical tool; a manipulator configured to support the surgical tool; a force/torque sensor configured to measure forces/torques applied to the surgical tool; and a control system configured to: obtain a predetermined tool path for the surgical tool; command the manipulator to perform an automated advancement of the surgical tool along the predetermined tool path in a first path direction and according to a predetermined feed rate; during the automated advancement of the surgical tool, receive an input from the force/torque sensor in response to forces/torques applied to the surgical tool by a user; evaluate an effect of the input from the force/torque sensor on the automated advancement of the surgical tool to determine an effective feed rate for the surgical tool with respect to the predetermined tool path; and determine a commanded action for the manipulator and the surgical tool with respect to the predetermined tool path based on the effective feed rate.

According to a fourth aspect, a method is provided of operating the robotic surgical system of the third aspect.

According to a fifth aspect, a robotic surgical system is provided that comprises: a surgical tool; a manipulator configured to support the surgical tool, the manipulator comprising a plurality of links and joints; a force/torque sensor configured to measure forces/torques applied to the surgical tool by a user; and a control system configured to: command the manipulator to perform an automated advancement of the surgical tool along a predetermined tool path according to a feed rate; and modify the feed rate based on the measured forces/torques applied to the surgical tool.

According to a sixth aspect, a method is provided of operating the robotic surgical system of the fifth aspect.

According to a seventh aspect, a robotic surgical system is provided that comprises: a surgical tool; a manipulator configured to support the surgical tool, the manipulator comprising a plurality of links and joints; a force/torque sensor configured to measure forces/torques applied to the surgical tool by a user; and a control system configured to: command the manipulator to perform an automated advancement of the surgical tool along a predetermined tool path according to a first path direction; and based on the measured forces/torques applied to the surgical tool, command the manipulator to advance the surgical tool along the predetermined tool path according to a second path direction that is opposite the first path direction.

According to an eighth aspect, a method is provided of operating the robotic surgical system of the seventh aspect.

Any of the described aspects can be combined in whole, in or part.

Any of the described aspects can be combined in whole, or in part, with any of the following implementations:

The effective feed rate can be greater than the predetermined feed rate. The effective path direction can be the first path direction. The commanded action can comprise automated advancement of the surgical tool along the predetermined tool path in the first path direction and according to the effective feed rate. Automated advancement of the surgical tool according to the effective feed rate can be based on a temporary input from the force/torque sensor. Automated advancement of the surgical tool according to the effective feed rate can be configured to continue absent input from the force/torque sensor. The effective feed rate can be less than the predetermined feed rate. The effective path direction can be the first path direction. The commanded action can comprise automated advancement of the surgical tool along the predetermined tool path in the first path direction and according to the effective feed rate or the predetermined feed rate. The effective path direction can be a second path direction being opposite the first path direction. The commanded action can comprise advancement of the surgical tool along the predetermined tool path in the second path direction and according to the effective feed rate. The commanded action can comprise simultaneously resisting advancement of the surgical tool in the second path direction, for example, by attempted automated advancement of the surgical tool in the first path direction. The control system can be configured to detect absence of the input from the force/torque sensor. In response, the control system can command the manipulator to initiate or restore the automated advancement of the surgical tool along the predetermined tool path in the first path direction and according to the predetermined feed rate or according to a prior effective feed rate. The predetermined tool path can comprise an end location. The control system can be configured to command the manipulator to perform the automated advancement of the surgical tool along the predetermined tool path in the first path direction and according to the predetermined feed rate or the effective feed rate to guide the surgical tool to the end location. The surgical tool can be a saw. The end location can be configured to align the saw with a cutting plane associated with a target site. The surgical tool can be a cutting burr or drill. The end location can be configured to align the cutting burr or drill with the start of a tool path associated with a target site or with a target axis associated with target site. The surgical tool can be configured to be activated to remove tissue. The control system can be configured to deactivate the surgical tool during the automated advancement of the surgical tool along the predetermined tool path. The control system can determine, based on the input from the force/torque sensor, a virtual acceleration vector. The control system can evaluate an effect of the virtual acceleration vector on the automated advancement of the surgical tool. The control system can determine the effective feed rate and the effective path direction for the surgical tool with respect to the predetermined tool path. To determine the virtual acceleration vector, the control system can model the surgical tool as a virtual rigid body comprising a virtual mass. The control system can compute a force projection to the virtual rigid body based on the forces/torques applied to the surgical tool. The control system can compute the virtual acceleration vector based on the force projection and the virtual mass. To determine the effective feed rate and the effective path direction for the surgical tool with respect to the predetermined tool path, the control system can compute a tool path direction based on a segment of the predetermined tool path on which the surgical tool is currently located. The control system can generate an acceleration projection along the predetermined tool path by computing a dot product of the tool path direction and the virtual acceleration vector. The control system can define virtual tool path constraints configured to limit movement of the surgical tool to be along the predetermined tool path. The control system can evaluate the effect of the virtual acceleration vector on the automated advancement of the surgical tool by being configured to simulate dynamics of the surgical tool in a virtual simulation based on the virtual tool path constraints, the predetermined feed rate and/or the virtual acceleration vector. The control system can command the manipulator to initiate the automated advancement in response to the force/torque sensor receiving the input from forces/torques manually applied to the surgical tool by the user.

Any of the implementations above can be combined in whole, or in part.

DESCRIPTION OF THE DRAWINGS

Advantages of the present disclosure will be readily appreciated as the same becomes better understood by reference to the following detailed description when considered in connection with the accompanying drawings.

DETAILED DESCRIPTION

I. Example System Overview

Figure 1:
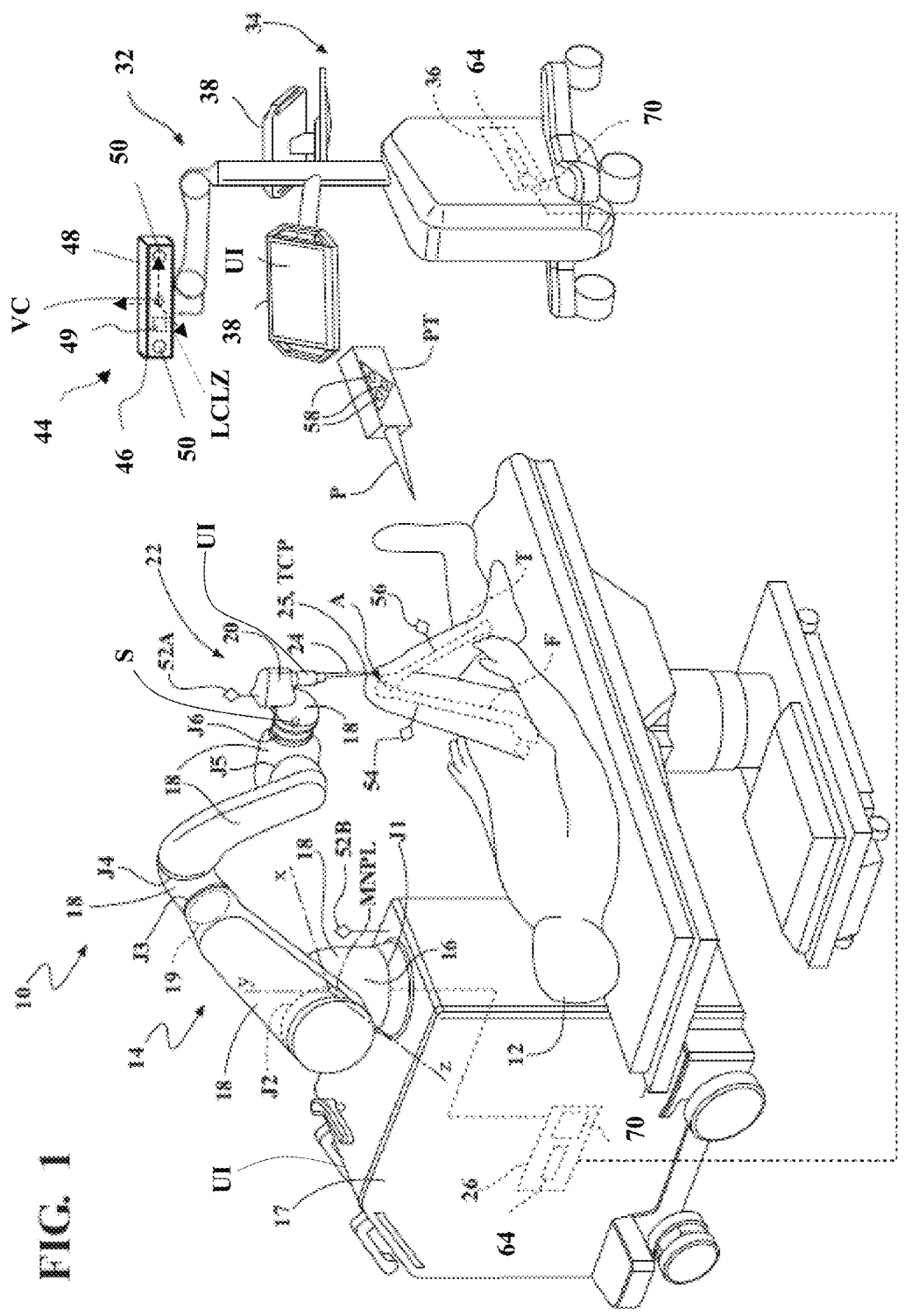
FIG. 1 is a perspective view of a robotic surgical system, according to one implementation.

Referring to FIG. 1, a robotic surgical system 10 is illustrated. The system 10 is useful for treating a surgical site or anatomical volume (A) of a patient 12, such as treating bone or soft tissue. In FIG. 1, the patient 12 is undergoing a surgical procedure. The anatomy in FIG. 1 includes a femur F and a tibia T of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0330429, entitled, "Prosthetic Implant and Method of Implantation," the disclosure of which is hereby incorporated by reference. The system 10 and techniques disclosed herein may be utilized to perform other procedures, surgical or non-surgical, or may be utilized in industrial applications or other applications where robotic systems are utilized.

The system 10 includes a manipulator 14. The manipulator 14 has a base 16 and plurality of links 18. A manipulator cart 17 supports the manipulator 14 such that the manipulator 14 is fixed to the manipulator cart 17. The links 18 collectively form one or more arms of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors at each joint J. Also, the manipulator 14 need not require rotary joints, but may alternatively, or additionally, utilize one or more prismatic joints. Any suitable combination of joint types is contemplated.

The base 16 of the manipulator 14 is a portion of the manipulator 14 that provides a fixed reference coordinate system for other components of the manipulator 14 or the system 10 in general. The origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the manipulator cart 17. In one example, the base 16 is defined at an intersection of the axes of joints J1 and J2. Thus, although joints J1 and J2 are moving components in reality, the intersection of the axes of joints J1 and J2 is nevertheless a virtual fixed reference pose, which provides both a fixed position and orientation reference and which does not move relative to the manipulator 14 and/or manipulator cart 17. In other examples, the manipulator 14 can be a hand-held manipulator where the base 16 is a base portion of a tool (e.g., a portion held free-hand by the user) and the tool tip is movable relative to the base portion. The base portion has a reference coordinate system that is tracked and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of conducting the functions described herein. The term processor is not intended to limit any embodiment to a single processor. The manipulator 14 may also comprise a user interface UI with one or more displays and/or input devices (e.g., push buttons, keyboard, mouse, microphone (voice-activation), gesture control devices, touchscreens, etc.).

A tool 20 couples to the manipulator 14 and is movable relative to the base 16 to interact with the anatomy in certain modes. The tool 20 is a physical and surgical tool and is, or forms part of, an end effector 22 supported by the manipulator 14 in certain implementations. The tool 20 may be grasped by the user. One possible arrangement of the manipulator 14 and the tool 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled, "End Effector of a Surgical Robotic Manipulator," hereby incorporated by reference.

The tool 20 can include an energy applicator 24 designed to contact and remove the tissue of the patient 12 at the surgical site. In one example, the energy applicator 24 is a bur 25. The bur 25 may be substantially spherical and comprise a spherical center, radius (r) and diameter. Alternatively, the energy applicator 24 may be a drill bit, a saw blade, an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the surgical site to perform the desired treatment. In some of the embodiments described herein, a spherical bur having a tool center point (TCP) will be described for convenience and ease of illustration but is not intended to limit the tool 20 to any particular form. In other examples, the tool 20 does not include an energy applicator 24. For example, the tool 20 can be a slotted cut guide for a saw, a guide tube for receiving another tool, or the like.

The tool 20 may comprise a tool controller to control operation of the tool 20, such as to control power to the tool (e.g., to a rotary motor of the tool 20), control movement of the tool 20, control irrigation/aspiration of the tool 20, and/or the like. The tool controller may be in communication with the manipulator controller 26 or other components. The tool 20 may also comprise a user interface UI with one or more displays and/or input devices (e.g., push buttons, keyboard, mouse, microphone (voice-activation), gesture control devices, touchscreens, etc.). For example, one of the user input devices on the user interface UI of the tool 20 may be a tool input (e.g., switch or other form of user input device) that has first and second input states (see FIG. 1). The tool input can be actuated (e.g., pressed and held) by the user to be placed in the first input state and can be released to be placed in the second input state. The tool 20 may have a grip on which the tool input is located. In some versions, the tool input is a presence detector that detects the presence of a hand of the user, such as a momentary contact switch that switches between on/off states, a capacitive sensor, an optical sensor, or the like. The tool input is thus configured such that the first input state indicates that a user is actively engaging the tool 20 and the second input state indicates that the user has released the tool 20. The tool input may be a continuous activation device, i.e., inputs that must be continually actuated to allow motion of the tool 20 in the manual mode or the semi-autonomous mode, depending on which user input is actuated. For example, while the user is continually actuating the tool input, and the manual mode is enabled, the manipulator 14 will move in response to the input forces and torques applied by the user and the control system 60 will enforce the virtual boundary 71 to protect the patient anatomy. When the tool input is released, input from the force/torque sensor S may be disabled such that the manipulator 14 no longer responds to the forces and torques applied by the user to the tool 20.

The manipulator controller 26 controls a state (position and/or orientation) of the tool 20 (e.g., the TCP) with respect to a coordinate system, such as the manipulator coordinate system MNPL. The manipulator controller 26 can control (linear or angular) velocity, acceleration, or other derivatives of motion of the tool 20. The tool center point (TCP), in one example, is a predetermined reference point defined at the energy applicator 24. The TCP has a known, or able to be calculated (i.e., not necessarily static), pose relative to other coordinate systems. The geometry of the energy applicator 24 is known in or defined relative to a TCP coordinate system. The TCP may be located at the spherical center of the bur 25 of the tool 20 such that only one point is tracked. The TCP may be defined in diverse ways depending on the configuration of the energy applicator 24. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 20 is not limited to a center point. For example, any suitable primitives, meshes, etc., can be utilized to represent the tool 20.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," hereby incorporated by reference. The navigation system 32 tracks movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. However, the input devices may include any one or more of push buttons, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In one example, the trackers include a pointer tracker PT, one or more manipulator trackers 52A, 52B, a first patient tracker 54, and a second patient tracker 56. In the illustrated example of FIG. 1, the manipulator tracker is coupled to the tool 20 (i.e., tracker 52A), the first patient tracker 54 is coupled to the femur F of the patient 12, and the second patient tracker 56 is coupled to the tibia T of the patient 12. In this example, the patient trackers 54, 56 are coupled to sections of bone. The pointer tracker PT is firmly affixed to a pointer P utilized for registering the anatomy to the localizer coordinate system LCLZ. The manipulator tracker 52A, 52B may be affixed to any suitable component of the manipulator 14, in addition to, or other than the tool 20, such as the base 16 (i.e., tracker 52B), or any one or more links 18 of the manipulator 14. The trackers 52A, 52B, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object with which it is associated.

Any one or more of the trackers may include active markers 58. The active markers 58 may include light emitting diodes (LEDs). Alternatively, the trackers 52A, 52B, 54, 56, PT may have passive markers, such as reflectors, which reflect light emitted from the camera unit 46. Other suitable markers not specifically described herein may be utilized.

The localizer 44 tracks the trackers 52A, 52B, 54, 56, PT to determine a state of each of the trackers 52A, 52B, 54, 56, PT, which correspond respectively to the state of the object respectively attached thereto. The localizer 44 may perform known triangulation techniques to determine the states of the trackers 52, 54, 56, PT, and associated objects. The localizer 44 provides the state of the trackers 52A, 52B, 54, 56, PT to the navigation controller 36. In one example, the navigation controller 36 determines and communicates the state the trackers 52A, 52B, 54, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. Navigation controller 36 has a central processing unit (CPU) and/or other processors, non-transitory memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of conducting the functions described herein. The term processor is not intended to limit any embodiment to a single processor.

Although one example of the navigation system 32 is shown that employs triangulation techniques to determine object states, the navigation system 32 may have any other suitable configuration for tracking the manipulator 14, tool 20, and/or the patient 12.

In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real-time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52A, 52B, 54, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such navigation system 32 examples may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally or alternatively comprise, fiber optic-based tracking, machine-vision tracking, and the like.

Figure 2:
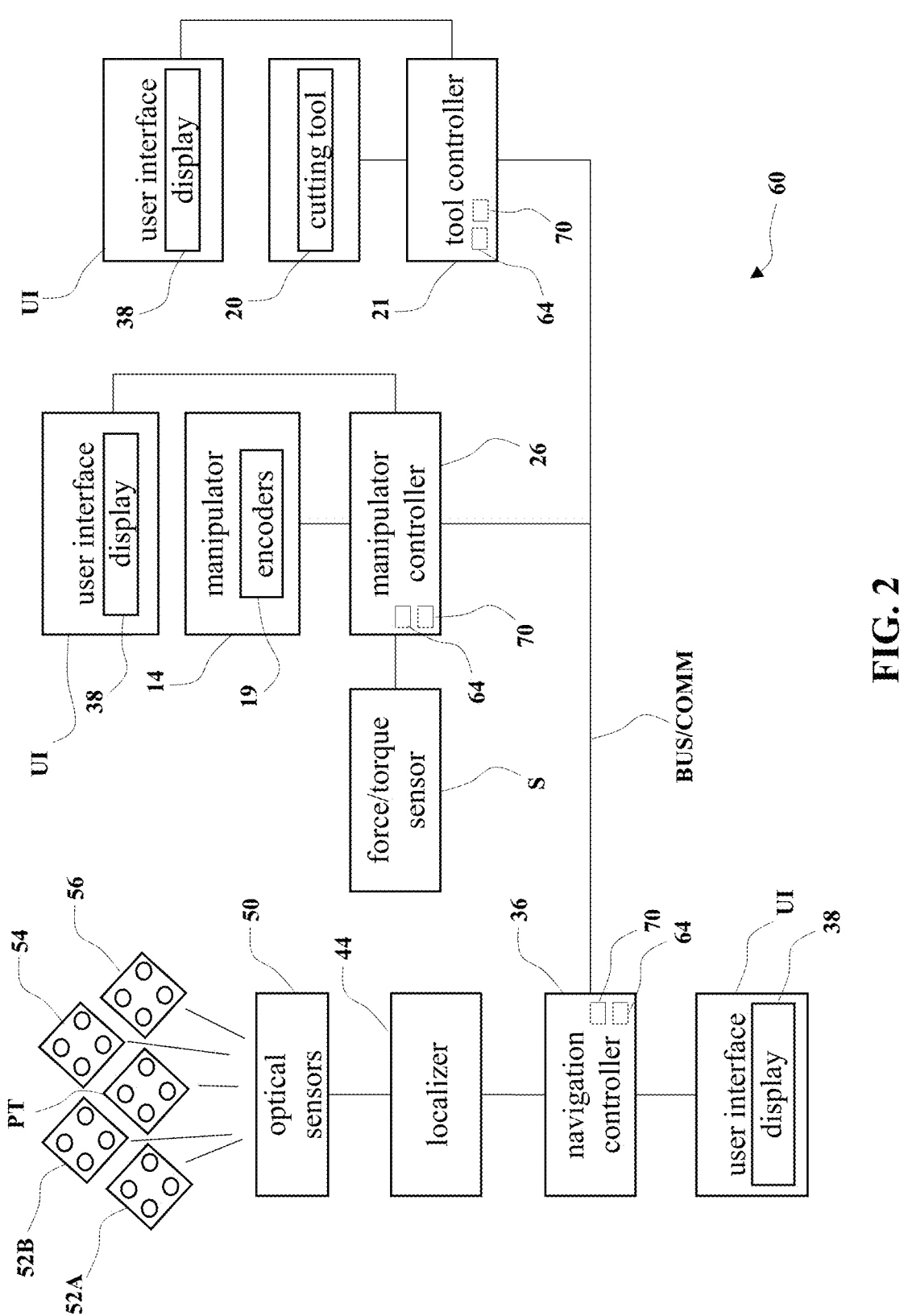
FIG. 2 is a block diagram of an example control system for controlling the robotic surgical system.

Referring to FIG. 2, the system 10 includes a control system 60 that comprises, among other components, the manipulator controller 26, the navigation controller 36, and the tool controller 21. The control system 60 further includes one or more software programs and software modules shown in FIG. 3. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for conducting the functions and methods described herein. The control system 60 may comprise the manipulator controller 26, the navigation controller 36, or the tool controller 21, or any combination thereof, or may comprise only one of these controllers. These controllers may communicate via a wired bus or communication network as shown in FIG. 2, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of conducting the functions described herein.

Figure 3:
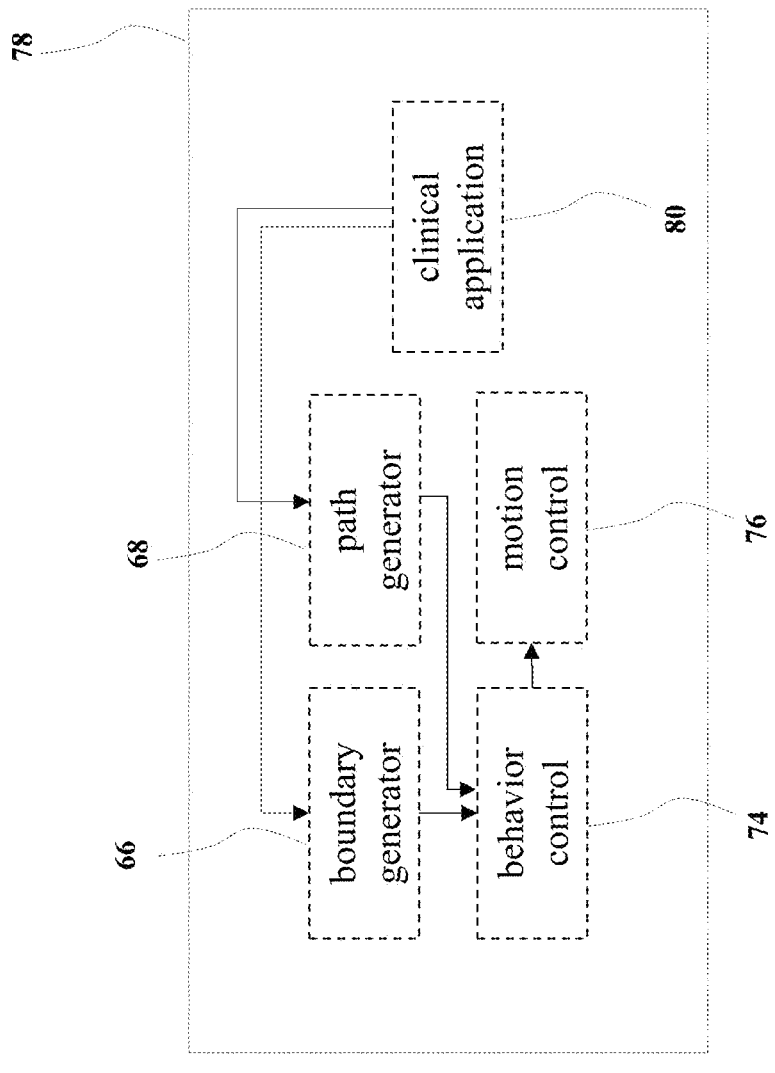
FIG. 3 is a functional block diagram of modules implemented by the control system, according to one implementation.
Figures 4, 5:
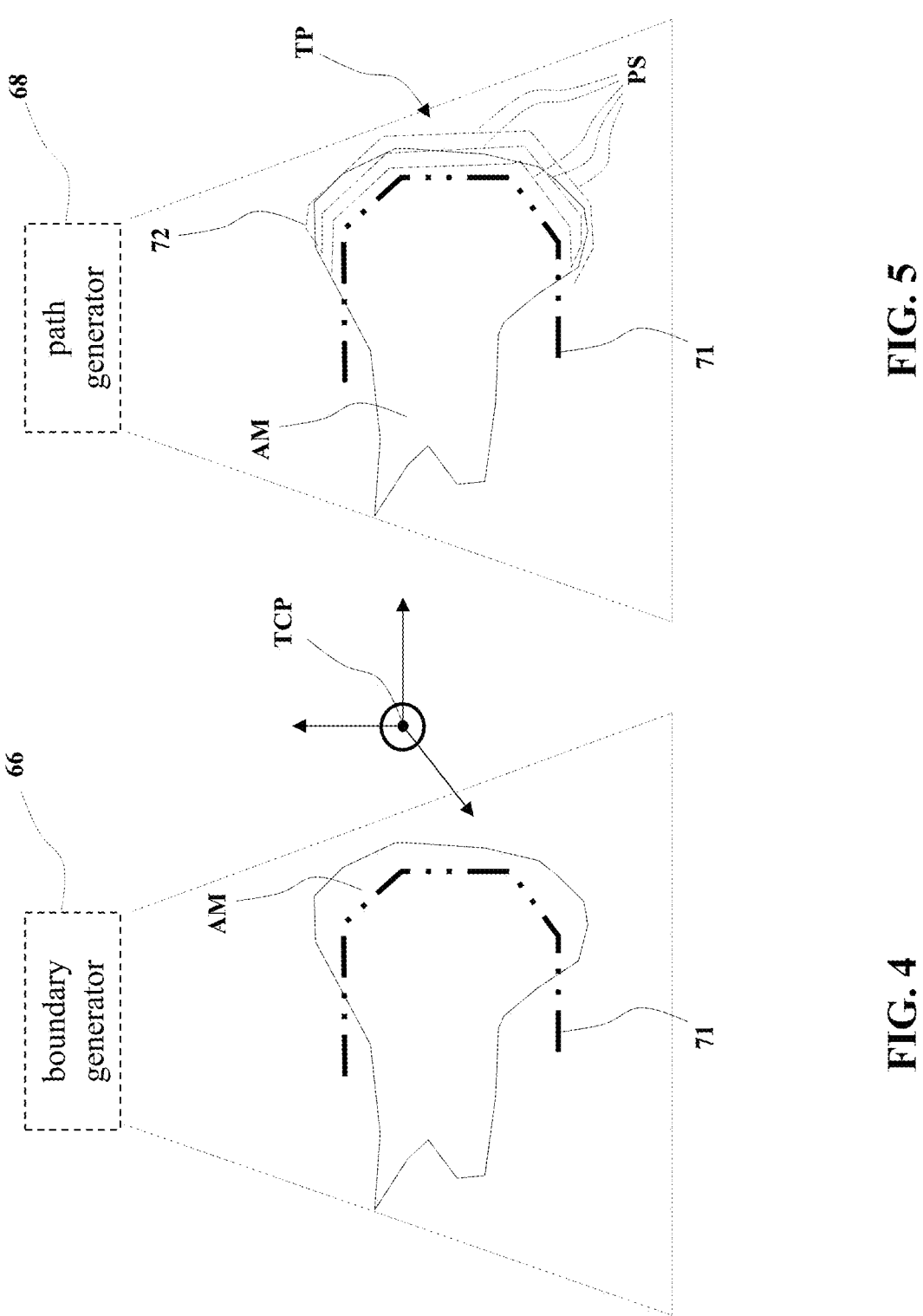
FIG. 4 illustrates an example output of a boundary generator.
FIG. 5 illustrates an example output of a path generator.

Referring to FIG. 3, the software employed by the control system 60 includes a boundary generator 66. As shown in FIG. 4, the boundary generator 66 is a software program or module that generates a virtual boundary 71 for constraining movement and/or operation of the tool 20. The virtual boundary 71 may be one-dimensional, two-dimensional, three-dimensional, and may comprise a point, line, axis, trajectory, plane, or other shapes, including complex geometric shapes. In some embodiments, the virtual boundary 71 is a surface defined by a triangle mesh. Such virtual boundaries 71 may also be referred to as virtual objects. The virtual boundaries 71 may be defined with respect to an anatomical model AM, such as a 3-D bone model. In the example of FIG. 4, the virtual boundaries 71 are planar boundaries to delineate five planes for a total knee implant, and are associated with a 3-D model of the head of the femur F. The anatomical model AM is registered to the one or more patient trackers 54, 56 such that the virtual boundaries 71 become associated with the anatomical model AM. The virtual boundaries 71 may be implant-specific, e.g., defined based on a size, shape, volume, etc. of an implant and/or patient-specific, e.g., defined based on the patient's anatomy. The virtual boundaries 71 may be boundaries that are created pre-operatively, intra-operatively, or combinations thereof. In other words, the virtual boundaries 71 may be defined before the surgical procedure begins, during the surgical procedure (including during tissue removal), or combinations thereof. In any case, the control system 60 obtains the virtual boundaries 71 by storing/retrieving the virtual boundaries 71 in/from memory, obtaining the virtual boundaries 71 from memory, creating the virtual boundaries 71 pre-operatively, creating the virtual boundaries 71 intra-operatively, or the like.

The manipulator controller 26 and/or the navigation controller 36 track the state of the tool 20 relative to the virtual boundaries 71. In one example, the state of the TCP is measured relative to the virtual boundaries 71 for purposes of determining haptic forces to be applied to a virtual rigid body model via a virtual simulation 88 so that the tool 20 remains in a desired positional relationship to the virtual boundaries 71 (e.g., not moved beyond them). The results of the virtual simulation 88 are commanded to the manipulator 14. The control system 60 controls/positions the manipulator 14 in a manner that emulates the way a physical handpiece would respond in the presence of physical boundaries/barriers. The boundary generator 66 may be implemented on the manipulator controller 26. Alternatively, the boundary generator 66 may be implemented on other components, such as the navigation controller 36.

Referring to FIGS. 3 and 5, a path generator 68 is another software program or module run by the control system 60. In one example, the path generator 68 is run by the manipulator controller 26. The path generator 68 generates a tool path TP for the tool 20 to traverse. The tool path TP may comprise a plurality of path segments PS, or may comprise a single path segment PS. The path segments PS may be straight segments, curved segments, combinations thereof, or the like. The tool path TP may be defined with respect to the manipulator 14 coordinate system MNPL, localizer coordinate system LCLZ, coordinate system of the tool 20, coordinate system of the anatomy, or any combination thereof. The tool path TP can be virtually attached to the coordinate system of the respective object such that if the object were to move, the tool path TP will correspondingly move. The tool path TP may be implant-specific, e.g., defined based on a size, shape, volume, etc. of an implant and/or patient-specific, e.g., defined based on the patient's anatomy. The tool path TP can be associated with a virtual model of the anatomy and the virtual model and tool path can be registered to the anatomy using the navigation system 32. The control system 60 can generate or obtain the tool path TP by storing/retrieving the tool path TP in/from memory, creating the tool path TP pre-operatively, creating the tool path TP intra-operatively, or the like. The tool path TP may have any 3D shape, or combinations of shapes, such as circular, helical/corkscrew, linear, curvilinear, combinations thereof, and the like.

In one implementation, the tool path TP is defined as a guidance or alignment path. In one example, the tool path TP is for guiding the tool 20 to move to a location that positions the tool 20 for a start of the surgical procedure, or step. For instance, if the tool 20 is a saw blade, the tool path TP may be configured to guide the saw blade to align to a cut plane associated with the anatomy. If the tool 20 is a cutting bur, the tool path TP may be configured to guide the cutting bur to a starting point in preparation for automated cutting. A lead-in path could be virtually connected from the starting point to another cutting path for removal of tissue. The tool path TP may also enable the tool 20 to move along a predefined path of motion for purposes of registering components of the manipulator 14 to the navigation system 32. The tool path TP can be registered to the anatomy using the navigation system 32 such that the tool path TP is virtually fixed to the anatomy. This way, the tool path TP location in space will automatically be updated to account for any movement of the anatomy.

In another implementation, as shown in FIG. 5, the tool path TP is defined as a tissue removal path. One example of the tissue removal path described herein comprises a milling path 72. The term "milling path" refers to the path of the tool

20 in the vicinity of the target site for milling the anatomy and is not intended to require that the tool 20 be operably milling the anatomy throughout the entire duration of the path. For instance, as will be understood in further detail below, the milling path 72 may comprise sections or segments where the tool 20 transitions from one location to another without milling. Additionally, other forms of tissue removal along the milling path 72 may be employed, such as tissue ablation, and the like. The milling path 72 may be a predefined path that is created pre-operatively, intra-operatively, or combinations thereof. In other words, the milling path 72 may be defined before the surgical procedure begins, during the surgical procedure (including during tissue removal), or combinations thereof.

One example of a system and method for generating the virtual boundaries 71 and/or the milling path 72 is described in U.S. Pat. No. 9,119,655, entitled, "Surgical Manipulator Capable of Controlling a Surgical Instrument in Multiple Modes," the disclosure of which is hereby incorporated by reference. In some examples, the virtual boundaries 71 and/or tool paths TP may be generated offline rather than on the manipulator controller 26 or navigation controller 36. Thereafter, the virtual boundaries 71 and/or tool paths TP may be utilized at runtime by the manipulator controller 26.

Referring to FIG. 3, two additional software programs or modules run on the manipulator controller 26 and/or the navigation controller 36. One software module performs behavior control 74. Behavior control 74 is the process of computing data that indicates the next commanded pose and/or orientation (e.g., pose) for the tool 20. In some cases, only the position of the TCP is output from the behavior control 74, while in other cases, the position and orientation of the tool 20 is output. Output from the boundary generator 66, the path generator 68, and a force/torque sensor S may feed as inputs into the behavior control 74 to determine the next commanded pose and/or orientation for the tool 20. The behavior control 74 may process these inputs, along with one or more virtual constraints described further below, to determine the commanded pose.

The second software module performs motion control 76. One aspect of motion control is the control of the manipulator 14. The motion control 76 receives data defining the next commanded pose from the behavior control 74. Based on these data, the motion control 76 determines the next position of the joint angles of the joints J of the manipulator 14 (e.g., via inverse kinematics and Jacobian calculators) so that the manipulator 14 is able to position the tool 20 as commanded by the behavior control 74, e.g., at the commanded pose. In other words, the motion control 76 processes the commanded pose, which may be defined in Cartesian space, into joint angles of the manipulator 14, so that the manipulator controller 26 can command the joint motors accordingly, to move the joints J of the manipulator 14 to commanded joint angles corresponding to the commanded pose of the tool 20. In one version, the motion control 76 regulates the joint angle of each joint J and continually adjusts the torque that each joint motor outputs to, as closely as possible, ensure that the joint motor drives the associated joint J to the commanded joint angle.

The boundary generator 66, path generator 68, behavior control 74, and motion control 76 may be sub-sets of a software program 78. Alternatively, each may be software programs that operate separately and/or independently in any combination thereof. The term "software program" is used herein to describe the computer-executable instructions that are configured to conduct the various capabilities of the technical solutions described. For simplicity, the term "software program" is intended to encompass, at least, any one or more of the boundary generator 66, path generator 68, behavior control 74, and/or motion control 76. The software program 78 can be implemented on the manipulator controller 26, navigation controller 36, or any combination thereof, or may be implemented in any suitable manner by the control system 60.

A clinical application 80 may be provided to manage user interaction. The clinical application 80 manages many aspects of user interaction and coordinates the surgical workflow, including pre-operative planning, implant placement, registration, bone preparation visualization, and post-operative evaluation of implant fit, etc. The clinical application 80 is configured to output to the displays 38. The clinical application 80 may run on its own separate processor or may run alongside the navigation controller 36. In one example, the clinical application 80 interfaces with the boundary generator 66 and/or path generator 68 after implant placement is set by the user, and then sends the virtual boundary 71 and/or tool path TP returned by the boundary generator 66 and/or path generator 68 to the manipulator controller 26 for execution. Manipulator controller 26 executes the tool path TP as described herein. The manipulator controller 26 may additionally create certain segments (e.g., lead-in segments) when starting or resuming machining to smoothly get back to the generated tool path TP. The manipulator controller 26 may also process the virtual boundaries 71 to generate corresponding virtual constraints as described further below.

The system 10 may operate in a manual mode, such as described in U.S. Pat. No. 9,119,655, incorporated herein by reference. Here, the user manually directs, and the manipulator 14 executes movement of the tool 20 and its energy applicator 24 at the surgical site. The user physically contacts the tool 20 to cause movement of the tool 20 in the manual mode. In one version, the manipulator 14 monitors forces and torques placed on the tool 20 by the user to position the tool 20. For example, the manipulator 14 may comprise the force/torque sensor S that detects the forces and torques applied by the user and generates corresponding input utilized by the control system 60 (e.g., one or more corresponding input/output signals). In some implementations, the user may be required to continually grasp a trigger or switch on the end effector to enable the force/torque sensor S that detects the forces and torques applied by the user.

The force/torque sensor S may comprise a 6-DOF force/torque transducer. The manipulator controller 26 and/or the navigation controller 36 receives the input (e.g., signals) from the force/torque sensor S. In response to the user-applied forces and torques, the manipulator 14 moves the tool 20 in a manner that emulates the movement that would have occurred based on the forces and torques applied by the user. Movement of the tool 20 in the manual mode may also be constrained in relation to the virtual boundaries 71 generated by the boundary generator 66. In some versions, measurements taken by the force/torque sensor S are transformed from a force/torque coordinate system FT of the force/torque sensor S to another coordinate system, such as a virtual mass coordinate system VM in which the virtual simulation 88 is carried out on the virtual rigid body model of the tool 20 so that the forces and torques can be virtually applied to the virtual rigid body in the virtual simulation 88 to ultimately determine how those forces and torques (among other inputs) would affect movement of the virtual rigid body, as described below.

The system 10 may also operate in a semi-autonomous or automated mode in which the manipulator 14 moves the tool 20 along the milling path 72 (e.g., the active joints J of the manipulator 14 operate to move the tool 20 without requiring force/torque on the tool 20 from the user). An example of operation in the automated mode is also described in U.S. Pat. No. 9,119,655, incorporated herein by reference. In some embodiments, when the manipulator 14 operates in the automated mode, the manipulator 14 is capable of moving the tool 20 free of user applied forces. In other words, the user does not need to physically contact the tool 20 to move the tool 20. Instead, the user may use some form of remote control to control starting and stopping of movement. For example, the user may hold down a button of the remote control to start movement of the tool 20 and release the button to stop movement of the tool 20.

The system 10 may also operate in a guided-manual mode, as described in U.S Patent Application Publication No. US 2020/0281676 A1, entitled "Systems and Methods for Controlling Movement of a Surgical Tool Along a Predefined Path", the contents of which are hereby incorporated by reference in their entirety. In the guided-manual mode, the user applies forces/torques to the force/torque sensor S and the applied forces/torques are utilized to determine how far to advance the tool 20 along the tool path TP. In the guided-manual mode, the tool 20 is constrained to the tool path TP in 2DOF normal to the tool path, but unconstrained in 1DOF tangential to the tool path TP. In effect, this enables the tool 20 to freely move along the tool path TP based on manual input, but the constraints guide the user by restricting the manual movement of the tool 20 to be along the tool path.

Described below is a hybrid/manual mode of operation, which combines aspects of the manual mode and automated mode.

II. Hybrid Automated/Manual Tool Guidance

Described herein are systems, methods, and techniques for guiding the tool 20 along the tool path TP using a hybrid automated/manual mode, which combines the benefits of manual mode and automated modes of operation. The system 10 commands the manipulator 14 to perform an automated advancement of the tool 20 along a predetermined tool path TP according to a predetermined feed rate. This predetermined feed rate can then be modified based on the measured forces/torques applied to the tool 20. In turn, the modified feed rate mimics the user's intentions and the hybrid mode empowers the user with a "hands-on" approach to dynamically increase or decrease the automated advancement of the tool 20, as desired. The automated advancement of the tool 20 can be a default state that relieves the user from fatigue associated with having to continually guide the tool 20, manually and physically. The default state can be predetermined or set based on the user's prior manual inputs. Meanwhile, the user can intervene at any time during automated advancement to manually tune the speed of the tool 20 along the tool path TP by applying forces to the tool 20. Additionally, hybrid mode control provides the user with a predictable or consistent response to give the user confidence in having control over the tool 20 when applying forces to the tool 20 because the tool 20 is constrained to the predetermined tool path TP.

In some conditions, the hybrid mode can enable the automated advancement to temporarily slow or halt in response to a collision between the tool 20 and an object colliding with tool 20 on the path TP. Once the object is removed from the path, automated advancement will continue. Hence, the hybrid mode need not be limited to requiring a user input. Whether or not user input is provided, the hybrid mode provides additional safeguards for automated movement of the tool 20.

This hybrid mode may be beneficial for tool paths TP that may be cumbersome or tiresome for the user to direct. As will be described below, the hybrid mode is advantageous for tool paths TP involved with guiding the tool 20 to an end location or end point EP or along a specific path of motion. This end point EP or path of motion may be relevant for a surgical procedure or may be for non-surgical purposes.

Figure 6:
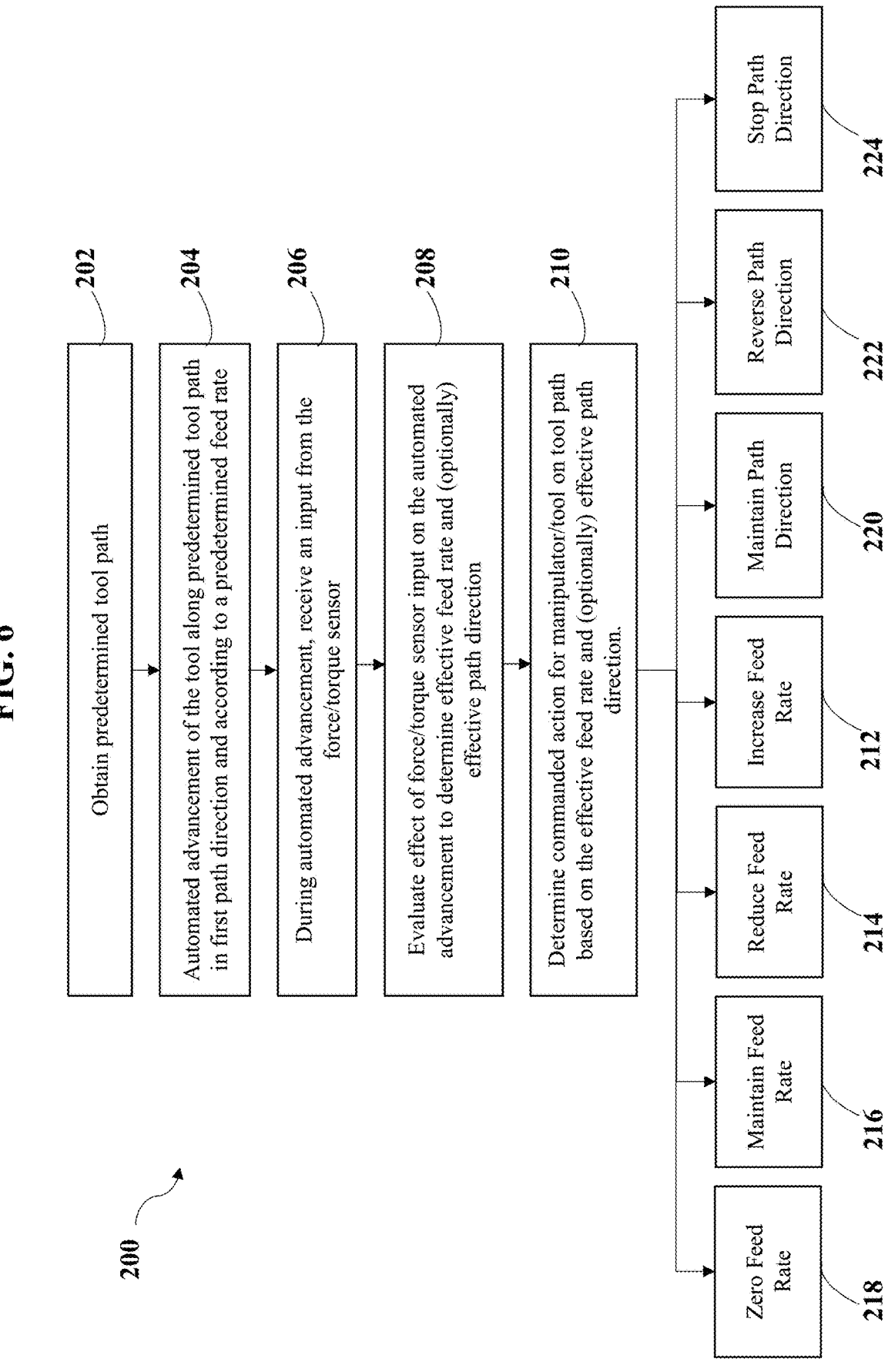
FIG. 6 is a flow chart of a method of steps involving hybrid mode control for guiding a tool along a tool path, according to one implementation.

With reference to FIG. 6, one example of implementing the hybrid mode can be summarized with method 200. At step 202, the control system 60 obtains a predetermined tool path TP for the surgical tool 20. The tool path TP can be like any of the implementations described above. At step 204, the control system 60 commands the manipulator 14 to perform an automated advancement of the surgical tool 20 along the predetermined tool path TP in a first path direction (PD1) and according to a predetermined feed rate PFR. The feed rate is a velocity at which the tool 20 traverses along the tool path TP. The predetermined feed rate PFR is a pre-defined velocity for automated advancement of the tool 20 for each path segment. Assuming there is no external input or obstruction, the tool 20 will continue to automatically advance along the tool path TP according to the predetermined feed rate PFR. The automated advancement may continue indefinitely, e.g., in a continuous path loop, or may automatically terminate once the tool 20 reaches the end point EP of the tool path TP. This automated advancement can initially be performed in the semi-autonomous or automated mode, as described above.

The predetermined feed rate PFR can be a constant velocity or can be dynamically changed based on various variables or sources, as described in International Patent Application No. PCT/US21/65334, entitled, "Robotic Systems and Methods for Mitigating Undesired Orientational Motion of Kinematic Components" the entire contents of which are hereby incorporated by reference. These variables include but are not limited to manual user adjustment to the feed rate, for example by using a control pendant, curvature of the path segment, and/or a collision with the virtual boundary 71. In one version, adjustment to PFR is performed by multiplying the PFR by any number of coefficients related to each of these variables. Each coefficient can be between 0 and 1.0. The coefficient value can change for each iteration of determining the PFR. Additional aspects of the predetermined feed rate PFR are described below.

At step 206, during the automated advancement of the surgical tool 20, the control system 60 receives an input from the force/torque sensor S in response to forces/torques applied to the surgical tool 20. These forces/torques may be applied by a user manually grasping the tool 20 and applying an external force to the tool 20. As such, the user applied forces implement aspects of the manual mode of operation described above. The hybrid mode is therefore realized through the manual mode intervention of automated advancement. In one implementation, the user applied force may be detected by the force/torque sensor S only in response to the user continually grasping a trigger or switch on the tool 20 or end effector while applying the force. This provides a confirmation of the user's intentions to apply the force. In another implementation, the user applied force may be detected by the force/torque sensor S without any confirmation trigger or switch on the tool 20, e.g., by the user simply pressing or pulling on the tool 20. In some cases, the control system 60 may apply thresholds or filters to the applied force to avoid movements that may considered to be unintentional or erratic.

Alternatively, the forces/torques may be applied by an object that collides with the tool 20 along the path TP. In either scenario, at step 208, the control system 60 can evaluate an effect of the input from the force/torque sensor S on the automated advancement of the surgical tool 20 to determine an effective feed rate EFR and an effective path direction EPD for the surgical tool 20 with respect to the predetermined tool path TP. Here, the control system 60 considers how the feed rate and path direction of the tool 20 relative to the tool path TP may be affected by the input from the force/torque sensor S. The details related to computing the effect of the manual force input on automated advancement will be described below.

At step 210, the control system 60 determines a commanded action for the manipulator 14 and/or the surgical tool 20 with respect to the predetermined tool path TP based on the effective feed rate EFR and effective path direction EPD. Examples of these commanded actions are shown in FIG. 6. Any of these commanded actions can be implemented individually or can be combined. With respect to the effective feed rate EFR, the commanded action can be increasing the feed rate (212), reducing the feed rate (214), maintaining the feed rate (216), or zeroing the feed rate (218). For any of these commanded actions, the effective feed rate EFR can be a tuning or altering of the predetermined feed rate PFR, or a replacement of the predetermined feed rate PFR. In other words, a new predetermined feed rate PFR can be derived from the effective feed rate EFR. When the feed rate is maintained (216), the effective feed rate EFR can be the same as the predetermined feed rate PFR or can be negligible or below a threshold so as to not be considered to have an effect on automated advancement of the tool 20. With respect to the effective path direction EPD, in many instances, the effective path direction EPD will be the same as the first path direction PD1. However, in some instances, the effective path direction EPD is opposite to the first path direction PD1. Hence, the commanded action can be maintaining the path direction (220), reversing the path direction (222), or stopping the tool 20 such that there is no directional movement of the tool 20 along the path TP. In any of these scenarios, the effective path direction EPD of the tool 20 is limited to a direction with respect to the tool path TP, rather than a direction off the tool path TP. In some configurations, it may not be required to compute how the input from the force/torque sensor S will affect the direction of the tool 20 relative to the tool path TP. For example, the control system 60 may limit the path direction to be forward, while prohibiting any reverse directional movement of the tool 20 along the path TP. Example computations involved with determining the effect of the force/torque sensor S input on automated advancement (feed rate and path direction) will be described below.

A. Example Use Cases of Hybrid Mode

The hybrid mode assists the user guiding the tool 20 along the tool path TP to a particular end point EP or along a specific path of motion. The hybrid control can be implemented for various use cases.

Figure 7:
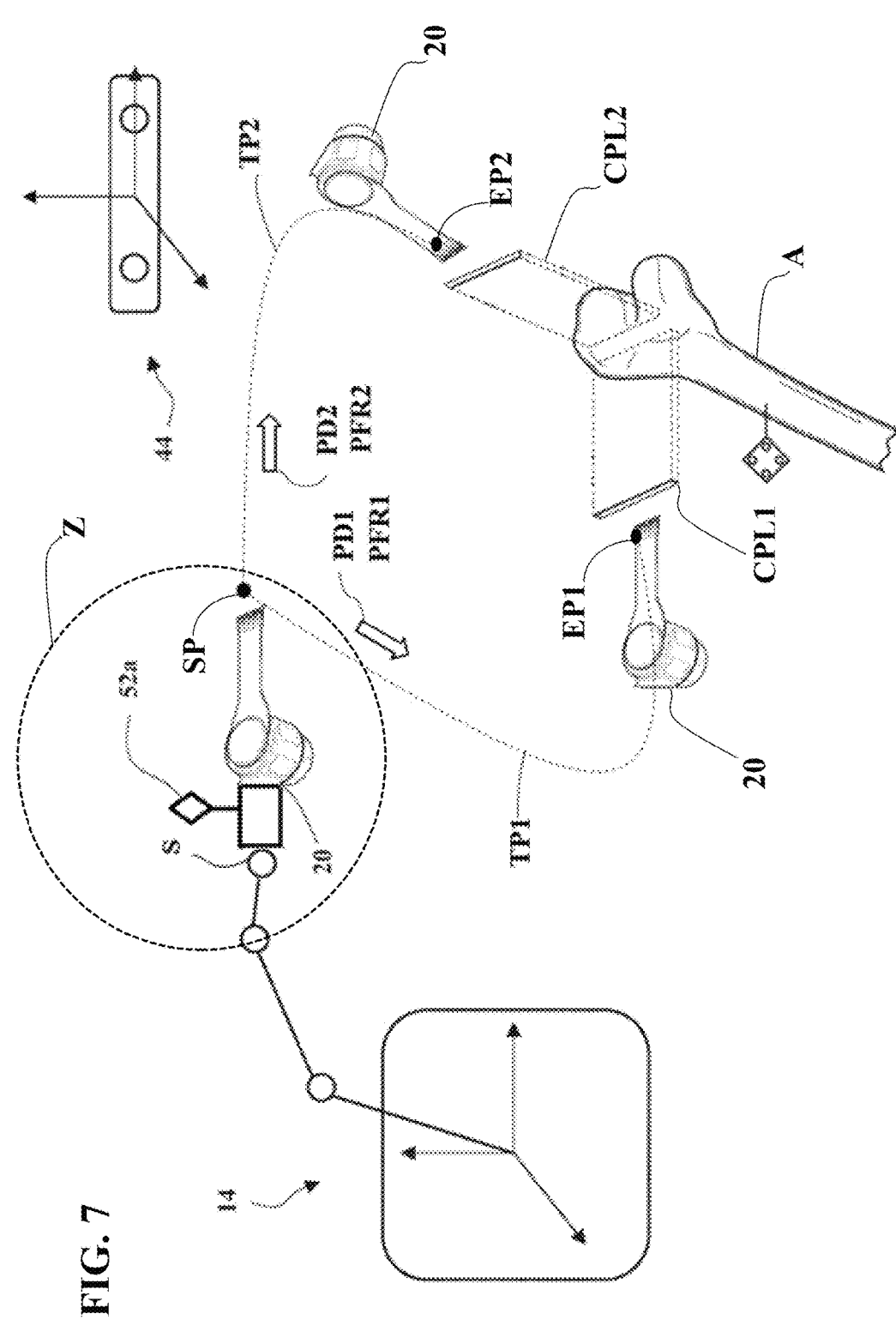
FIG. 7 illustrates an example of automated advancement of the tool, e.g., a saw, along various tool paths for guiding the saw to respective cut planes associated with the anatomy.

In one example, as shown in FIG. 7, the automated advancement aspect of the hybrid mode may be utilized for aligning a saw blade to one or more cut planes CPL1, CPL2 associated with the anatomy (A). The cut planes CPL may be implemented as virtual boundaries 71 generated by the boundary generator 66 for constraining movement of the saw to be along the cut plane CPL. The cut planes CPL may be registered to the anatomy (A) using the navigation system 32. The cut planes CPL may be implemented for total knee arthroplasty procedures and may include five or more cuts on the femur and one cut on the tibia. Several tool paths TP1, TP2, may be generated by the control system 60 between a current or specified starting point SP of the tool 20 that is remote from the anatomy (A). In preparation for each cut, the tool 20 is commanded to automatically advance along the respective tool path TP until the tool 20 reaches a respective end point, EP1, EP2. The end point EP in this example is chosen to align the plane of the saw blade to the respective cut plane CPL at a specified distance from the anatomy (A) (e.g., 100 mm). Therefore, in this example, the automated advancement aspect of hybrid mode control is not for removing tissue, but for assisting the user in guiding the tool 20 to the various cut planes CPL. The control system 60 defines a predetermined feed rate PFR and path direction PD for the tool 20 with respect to each tool path TP. In one implementation, the predetermined feed rate PFR is constant throughout the tool path TP. However, the predetermined feed rate PFR may be the same or different among the tool paths TP. Also, the predetermined feed rate PFR may be the same or different for various portions or segments of one tool path TP. For example, for path segments at one portion of the tool path TP, the predetermined feed rate PFR may have lower velocity to smoothly ramp up the tool 20 speed until it eventually reaches a terminal velocity for the remaining portions of the tool path TP. Also, the predetermined feed rate PFR may be configured to be faster or slower depending on the length of the tool path TP to avoid delays in moving the tool 20 to the end point EP1 or to provide a better user experience. Although not shown in FIG. 7, during automated advancement to these various cut planes (CP), the user can apply forces to the tool 20 to increase or decrease the feed rate of the tool 20 to their liking.

In some instances, the starting point SP of the tool 20 from which the tool path TP begins may be defined by a zone (Z), as shown in FIG. 7. The zone (Z) may be a virtual 3D region, such as a sphere, in which the tool 20 can virtually enter. The starting point SP can be a fixed location within the zone (Z) or can be defined by any current location of the tool 20 or TCP within the zone (Z). Once the tool 20 is detected to be within the zone (Z), the user may be prompted by the clinical application 80, e.g., on user interfaces UI or displays, to confirm the cut plane CPL, tool path TP, and/or the commencement automated advancement using the hybrid mode.

In another example, the hybrid mode may be utilized for guiding a cutting bur to an end point EP relative to the anatomy (A). This end point EP may be the start of another tool path TP that will be utilized for automated milling of the anatomy (A) using the automated or semi-autonomous mode. Alternatively, the end point EP can be a specified distance from the anatomy (A) (e.g., 100 mm) in preparation for later enabling the tool 20 to be utilized for removing tissue using the manual mode. In either case, the hybrid mode enables the user to apply forces to the tool 20 to change the feed rate of the tool 20 along the path. For example, the user may feel reluctant to allow the automated advancement of a sharp cutting tool towards the anatomy (A) and may use the hybrid mode to apply some control during automated advancement to selectively slow the feed rate of the tool 20.

The hybrid mode may also be utilized for aligning a tool (such as a screwdriver or drill) or guide tube to a target trajectory relative to the anatomy (A). This technique may be valuable in preparation for pedicle cannulation or insertion, drilling peg holes in the anatomy for receipt of an implant, aligning an impactor or reamer for total hip surgery, etc. Again, the hybrid mode control may be utilized for different reasons depending on the use cases. In this example of a target trajectory, the user may apply forces during automated advancement to selectively increase the feed rate to allow the tool 20 to reach the target trajectory more quickly.

For the above examples involving the anatomy (A) and cutting tool, the control system 60 may deliberately deactivate the tool 20 such that the tool 20 is not energized and cannot remove tissue during automated advancement. Tool deactivation may be useful in situations where the tool path TP is utilized for assisting the user in guiding the tool 20 towards the anatomy (A) in preparation for surgery. Deactivating the tool 20 in this manner can help to avoid accidental injury because the hybrid mode can involve the user selectively grasping the tool 20 and applying forces to a tool 20 that is automatically moving. For situations in which the hybrid mode uses the tool path TP for removing tissue, the tool 20 will be in an active state.

Additionally, the hybrid mode is useful for tool paths TP that are non-surgical. One example is a tool path TP involved with performing a navigation registration of the manipulator 14. In this scenario, the tool 20 is automatically moved along a predetermined tool path TP (such as a pendulum or elliptical path). Trackers 52A attached to, or integrated with, the tool 20 can be tracked by the navigation system 32 during movement along the tool path TP. Simultaneously, the base tracker 52B can be tracked by the navigation system 32. Therefore, the relationship between the tool tracker 52A and the base tracker 52B is known. However, the relationship between the base tracker 52B and the base 16 of the manipulator 16 may not be known due to manual setup of the base tracker 52B by a technician. To determine the relationship between the base tracker 52B and the base 16, the tracked data associated with the tool 20 is fused with kinematic data from movement of the manipulator 14 joints (J) to determine a transform from the base tracker 52B to the base 16. Once this transform is determined, the registration of the manipulator 14 is complete. With the hybrid mode, the user may intervene during the manipulator registration processes to slow the speed of automated tool movement along the path to prevent the possibility of the tool 20 and/or manipulator 14 colliding with an object, including the manipulator itself. The user may also apply forces to the tool 20 to reverse the path direction for enabling the navigation system 32 to recapture additional tracking data.

In some cases, the tool path TP can be dynamically or intraoperatively defined using the navigation pointer (P) tracked by the navigation system 32. The user can move the pointer (P) to any location or along a path of motion. The location or movement of the pointer tip is then tracked by the navigation system 32 and the tool path generator 68 can generate the tool path TP or locate points of the tool path TP based on the pointer tip movement. This pointer technique can be utilized to identify the end point EP of the tool path. The end point EP can be like the example end points EP described above, a point on the anatomy, or any point desired by the user. This pointer technique can also be utilized to identify the starting point of the tool path TP. Furthermore, any number of points between the starting and ending points can be defined using the pointer (P). For example, the user may utilize the pointer (P) to digitize six points in space. The tool path generator 68 can then interpolate the points to approximate or generate the tool path TP which the user intended to form along the respective points. Other uses cases of the hybrid mode are possible beyond those described above.

B. Hybrid Mode Initialization

Many techniques are contemplated for determining the user's intention to initiate the hybrid mode. In one instance, the automated advancement of the tool 20 in the hybrid mode can be initiated automatically once the tool 20 reaches the zone (Z) or starting point SP. In some cases, the user may be required to apply a force/torque to the tool 20 to manually initiate the automated advancement. Alternatively, the user may be required to press a trigger or button the tool 20 or end effector and apply force to initiate the automated advancement. The hybrid mode can also be initialized at the will of the user using any type of user interface, such as a remote control or pendant coupled to the manipulator 14.

Also, automated advancement in the hybrid mode can start from any state of the tool 20 and can transition from/to any prior mode of operation. For example, automated advancement can begin after the tool 20 is initially at rest, can transition from/to manual mode movement of the tool 20 or can transition from/to the automated or semi-autonomous mode. In addition, automated advancement in the hybrid mode can transition to/from the guided-manual mode.

Also, the tool 20 may be off the tool path when automated advancement in the hybrid mode is initiated. In one example, the user may apply force/torque to the tool 20 in the manual mode and when the tool is off the tool path and the system may gradually transition the user's applied force into hybrid advancement along the tool path. For instance, the velocity vector from the user's applied force may be gradually blended based on time and/or distance into a desired velocity vector from the predetermined feed rate PFR for automated advancement. As this blending continues the tool 20 will move towards the tool path and may accelerate or decelerate based on the magnitude and direction of the vectors and the gradual blending thereof.

In some cases, the control system 60 can detect the direction of force/torque manually applied to the tool 20 by the user in the manual mode and determine whether the direction of force/torque is towards the tool path TP or intersecting the tool path TP. If so, the manipulator 14 can be controlled to move the tool 20 to the tool path TP and thereafter initialize the hybrid mode. In some instances, this movement is implemented using attractive haptics. Such attraction can be implemented by guide handler of the control system 60 obtaining a current state of the tool (off the tool path) and a target state for the tool 20 (on the tool path) and generating one or more virtual constraints based on the current and target states. The control system 60 can implement a constraint solver 86 (described further below) to calculate a constraint force adapted to attract the tool 20 toward the target state on the tool path TP from the current state based on the one or more virtual constraints. The control system 60 implements the virtual simulator 88 to simulate dynamics of the tool in the virtual simulation 88 based on input from the one or more sensors and based on the constraint force to output a commanded pose CP. The control system 60 then commands the manipulator 14 to move the tool 20 to the path based on the commanded pose CP to thereby provide haptic feedback to the user that guides the user toward placing the tool 20 at the target state in preparation for hybrid mode advancement along the tool path TP. In one example, once an initial force on the tool is detected, the system may gradually increase the force of the virtual constraints to move the tool 20 to the path. The increase of virtual constraint force may be implemented over a predetermined duration and/or may be based on the relative distance between the tool and the path. Examples of attractive haptics which can be utilized to guide the tool to the tool path can be like that described in U.S. patent application Ser. No. 17/701,989, entitled "Systems and Methods for Guiding Movement of a Tool", the entire contents of which are incorporated by reference herein.

In other cases, the path generator 68 can dynamically generate a lead-in path from the current state of the tool 20 (off the path) to the starting point of the tool path TP utilized by the hybrid mode. The lead-in path can be generated in response to a user input, e.g., using any of the described user interfaces UI. The tool 20 can move along the lead-in path using the manual or automated mode. Once the tool 20 reaches the starting point of the hybrid mode tool path TP, the tool 20 can either immediately begin automated advancement or may pause at the starting point awaiting user confirmation to initialize hybrid mode advancement.

C. Hybrid Mode Computation Examples

As described above, the hybrid mode involves receiving an input from the force/torque sensor S in response to forces/torques applied to the tool 20 during the automated advancement of the tool 20. The control system 60 evaluates an effect of the input from the force/torque sensor S on the automated advancement of the tool 20 to determine the effective feed rate EFR, and optionally, an effective path direction EPD for the tool 20 with respect to the predetermined tool path TP. Described in this section are example computations involved with evaluating the effect of the force/torque sensor S input on the automated advancement of the tool 20.

Figures 8, 9:
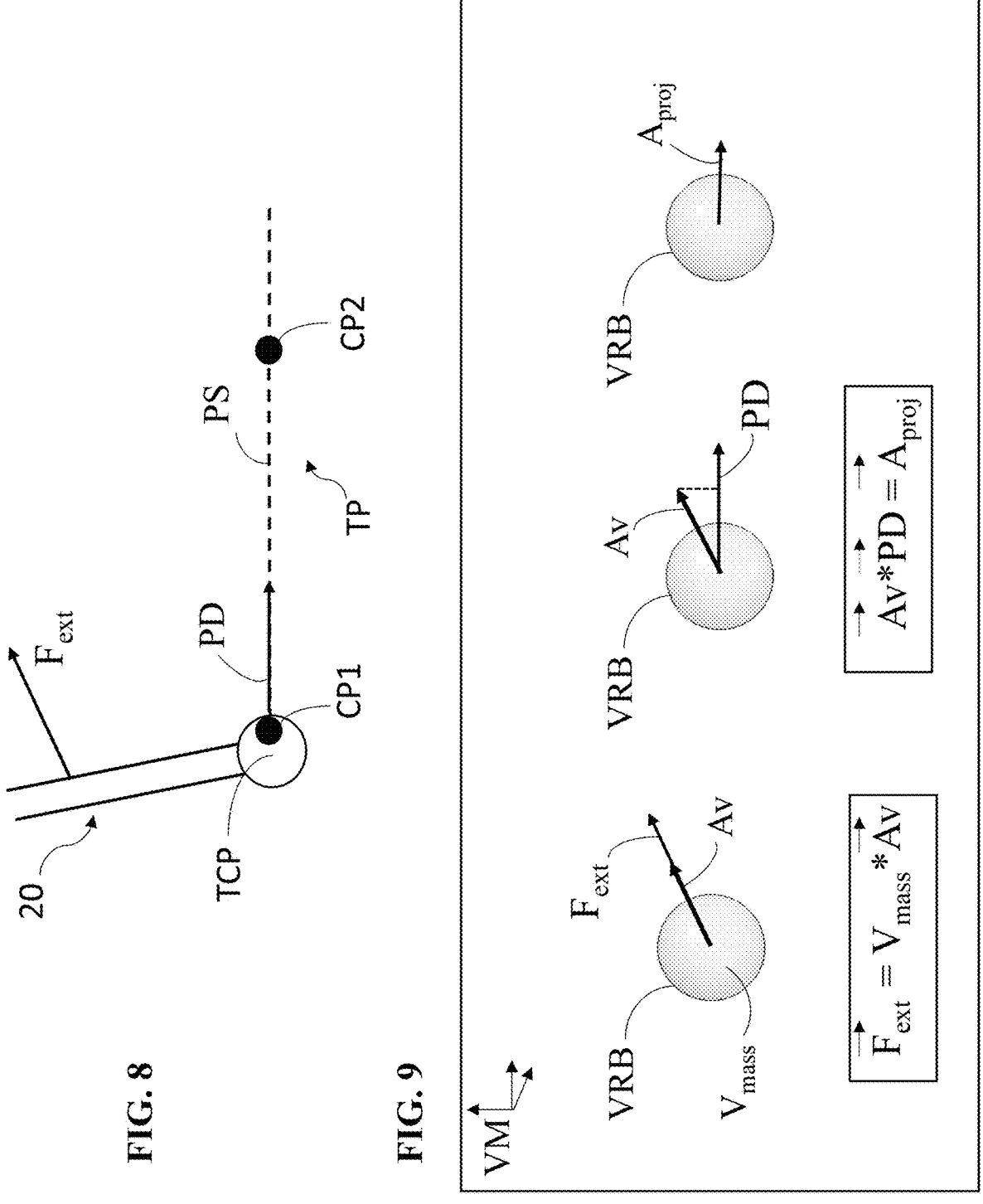
FIG. 8 is a diagram illustrating the tool on a segment of the tool path wherein an external force (Fext) is applied to the tool, according to one example.
FIG. 9 is a diagram illustrating a virtual rigid body model of the tool wherein a series of computations are performed to compute an acceleration projection along the tool path based on the external force (Fext).

FIG. 8 illustrates an example where the input from the force torque sensor S is represented as a vector Fext, shown relative to the tool 20 on the path TP. The location of Fext in FIG. 8 is provided only as an example and may have different magnitude and/or direction depending on the nature of the applied forces/torques. In this example, it is assumed that Fext has components in a forward direction along the tool path TP. In FIG. 8, only one path segment PS of the tool path TP is shown for simplicity. The tool 20 is currently located on the tool path TP such that the TCP is at a prior commanded pose CP1. The path segment PS is defined from the prior commanded pose CP1 to the next commanded pose CP2.

To evaluate the effect of the Fext on the automated advancement of the tool 20, the control system 60 may be configured to determine a virtual acceleration vector (Av) based on the force/torque sensor S input, and more specifically Fext. The virtual acceleration vector (Av) represents the virtual acceleration derived from the Fext. FIG. 9 illustrates example computational steps involved with respect to the virtual rigid body VRB model of the tool 20 or TCP. As described above, the virtual rigid body VRB is utilized in the virtual simulation 88 so that the forces and torques can be virtually applied to the virtual rigid body VRB (in the virtual mass coordinate system VM). The virtual simulation 88 is utilized to determine how those forces and torques (among other inputs) would affect movement of the virtual rigid body VRB. Alternatively, or additionally, the TCP of the tool 20 can be evaluated by the virtual simulation 88 so that the forces and torques can be virtually applied to the TCP (in the coordinate system of the TCP). To determine the virtual acceleration vector (Av), the control system 60 computes or transforms the force projection Fext to the virtual rigid body VRB in coordinate system VM. The control system 60 utilizes the known virtual mass (Vmass) of the virtual rigid body VRB to solve for F=mA, where 'F' is Fext, 'In' is the virtual mass (Vmass) of VRB and 'A' is the virtual acceleration vector (Av). The result of the computation as shown in the example of FIG. 9 is the virtual acceleration vector (Av) having the same direction, but a lesser magnitude, than Fext. However, depending on the Vmass and Fext, the virtual acceleration vector (Av) could alternatively have a different direction, or the same or greater magnitude as Fext.

Once the virtual acceleration vector (Av) is determined, the control system 60 computes a tool path direction PD based on a segment PS of the tool path TP on which the tool 20 is currently located, as shown in FIG. 8. In this case, it is assumed that the tool path TP is comprised of several discrete path segments PS, each of which are linear. Hence, the path direction PD can be computed with a unit vector defined from the start to the end of the path segment PS, or from the prior commanded pose CP1 to the next commanded pose CP2. In other situations, the path segment PS may be curved or curvilinear. In such instances, the tool path direction PD may be derived using a similar unit vector (from segment start to end) or using any type of approximation, such as taking an average direction from tangential components of the curved segment, approximating a line through the curved segment, or the like. The path direction PD is applied, or transformed, to the VM coordinate system of the virtual rigid body VRB, as shown in FIG. 9.

Having obtained the virtual acceleration vector (Av) and the path direction PD, the control system 60 computes a dot product of these vectors to generate an acceleration projection (Aproj), as also shown in FIG. 9. The acceleration projection (Aproj) has magnitude and direction, both of which can influence the feed rate and the path direction for the tool 20. The acceleration projection (Aproj) may be understood as the tool path component of the virtual acceleration derived from Fext.

Figure 10:
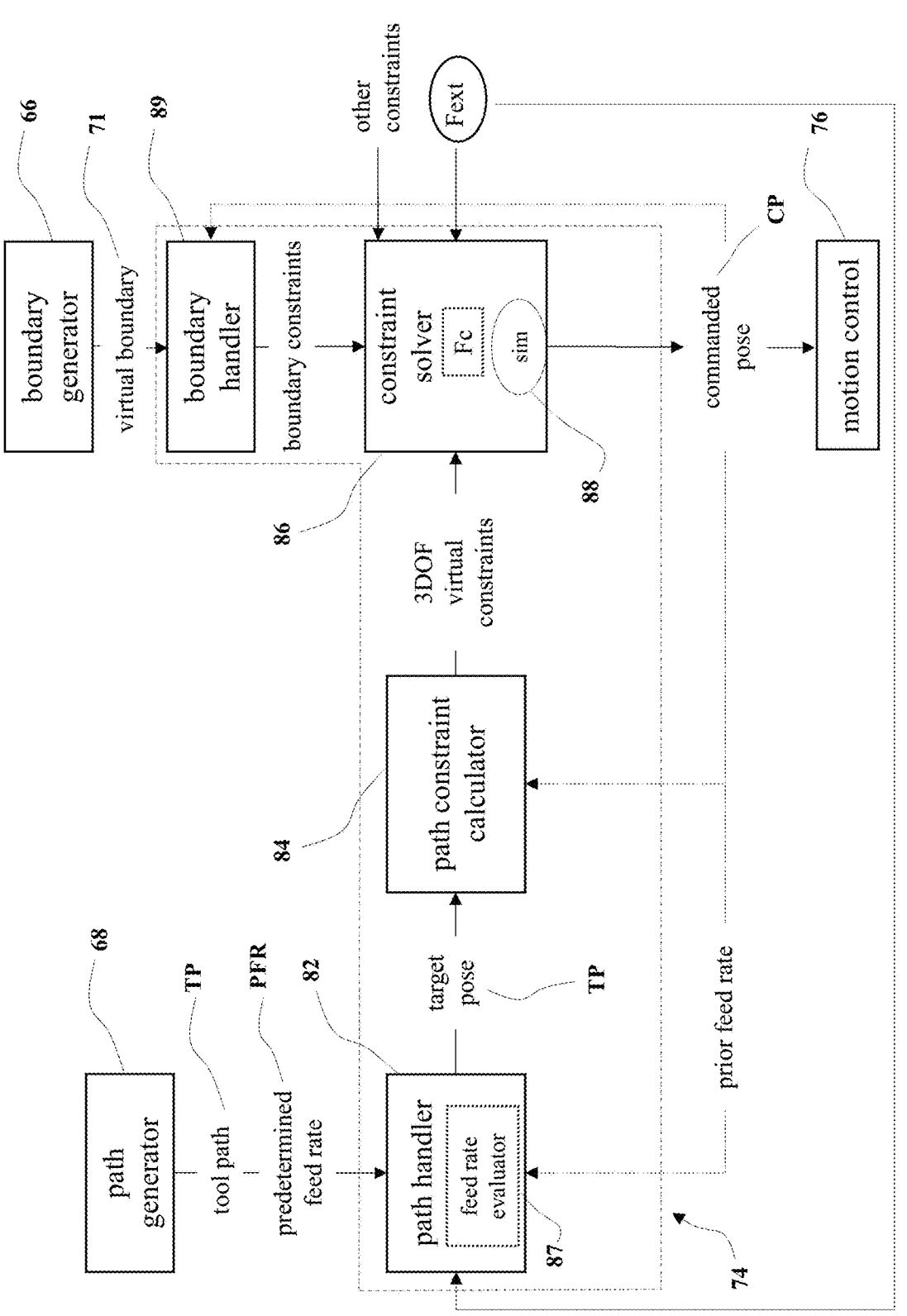
FIG. 10 is a block diagram of modules operable by the behavior controller of the control system for implementing aspects of the hybrid control mode.

FIG. 10 illustrates a block diagram of the modules and processes executed by the control system 60 for implementing the hybrid control mode. In this example, the behavior control 74 comprises the path handler 82, the path constraint calculator 84, the constraint solver 86, and the virtual simulator 88. The path handler 82, path constraint calculator 84, constraint solver 86, and the virtual simulator 88 each comprises executable software stored in a non-transitory memory of any one or more of the aforementioned controllers and implemented by the control system 60.

In this version, the path handler 82 can receive several inputs: the predetermined tool path TP and predetermined feed rate PFR associated with the tool path TP (or segments), Fext from the force/torque sensor S input, and the previous commanded pose CP and previous feed rate of the tool 20 or TCP. The predetermined feed rate PFR represents the default feed rate for automated advancement of the tool 20 for each of the path segments, including the current path segment. In some cases, the predetermined (first) path direction PD1, which is utilized for automated advancement, can be inputted into the path handler 82. The predetermined path direction PD1 can be derived from the predetermined feed rate PFR, implicit in the PFR, or provided with data associated with the PFR.

The path handler 82 can processes any number of these inputs to determine a target pose TP for the tool 20. The target pose TP has its origin located on the tool path TP and is the pose at which it is desired to move the TCP of the tool 20. Ideally, the next commanded pose CP coincides with the target pose TP. However, in certain cases, the next commanded pose CP may not coincide with the target pose TP.

The path handler 82 implements a feed rate evaluator 87 module or sub-module to execute certain aspects of the hybrid control mode. At each iteration of the process shown in FIG. 10, which may be carried out at any suitable frame rate (e.g., every 125 or 250 microseconds), the feed rate evaluator 87 evaluates different feed rate inputs for the current path segment and applies predetermined rules for determining the (final) effective feed rate EFR which defines how far the tool should move along the current path segment PS. More specifically, the feed rate evaluator 87 obtains or computes an initial feed rate for the tool 20 along the current path segment and determines whether or not to modify or tune the initial feed rate based on Fext. The path handler 82 may or may not receive the external force Fext input depending on whether or not an external force/torque was applied to the tool 20. Assuming that automated advancement has previously commenced and there was no prior or current input from the force/torque sensor S, the initial feed rate will be defaulted to the predetermined feed rate PFR (automated speed). However, if there was a prior input from the force/torque sensor S, the initial feed rate may be based on a prior effective feed rate EFR (hybrid mode speed), which may or may not be a modified/tuned version of the predetermined feed rate PFR. The effective feed rate EFR could be combined with other feed rate sources before determining the location of the target pose TP, such as the feed rate sources described above and described in U.S. Pat. No. 9,566,122, hereby incorporated herein by reference.

When an external force/torque is currently applied to the tool 20, Fext is inputted to the path handler 82 for the current iteration of the process. For the current time step, the path handler 82 computes the acceleration projection (Aproj), as described above. The path handler 82 can integrate the acceleration projection (Aproj) to obtain an offset feed rate. In other words, the offset feed rate is derived from the acceleration projection (Aproj), which is derived from Fext. The path handler 82 can also double integrate the acceleration projection (Aproj) to obtain the displacement along the tool path TP and the target pose TP or next commanded pose CP. The offset feed rate is another input to the feed rate evaluator 87. The offset feed rate is a potential offset to the initial feed rate. As will be described below, there are rules which may dictate that the offset feed rate should not applied to the initial feed rate. There are also situations where the offset feed rate may override or replace the initial feed rate. The effects of Fext on the initial feed rate can be computed using distance, velocity and/or acceleration, or combinations thereof. For example, an initial acceleration and offset acceleration may be utilized instead of an initial feed rate and offset feed rate.

Having obtained the initial feed rate and offset feed rate, the path handler 82 and/or feed rate evaluator 87 can compute the effective feed rate EFR using any form of the uniform acceleration equations, such as $\Delta d=(Vo+Vf/2)/t$, where Vo is the velocity of the initial feed rate, Vf is the velocity of the offset feed rate, t is the current time step duration, and $\Delta d$ is representative of the distance the tool 20 will travel along the path TP according to effective feed rate EFR. Other acceleration equations can be utilized, such as $Vf=Vo+at$, where a is the acceleration projection (Aproj). In some implementations, the offset feed rate can be realized as a coefficient within the unit value range of −1 to 0 to +1 for scaling or modifying the initial feed rate. The coefficient value can be derived from a look-up table correlated with values of Fext.

In some cases, such as when automated advancement is initialized and there is no external force being applied to the tool 20, the feed rate is gradually accelerated until the predetermined feed rate PFR is reached. Here, the acceleration component of Vf=Vo+at may be selected as a default acceleration value or range of values instead of the acceleration projection (Aproj). Once the predetermined feed rate PFR is reached, the acceleration component may be zeroed or removed from the equation until an external force is detected.

The offset feed rate, acceleration projection (Aproj), and/or Fext can be computed so that a positive value is in a forward path direction and a negative value is in a negative path direction. The integrations can thus be performed in a manner yielding the direction of the effective feed rate EFR, or the effective path direction EPD. For example, a negative distance indicates to move backwards along the tool path TP. In some cases, it may not be desired to allow the user to move backwards along the tool path TP. In that case, if a negative distance is computed, it may be limited at zero or disregarded.

Assuming Fext was applied, the path handler 82 will have obtained the effective feed rate EFR and effective path direction EPD. The path handler 82 then steps iteratively within a time step along the tool path TP, one path segment PS at a time, until the accumulated distance stepped along the tool path TP (e.g., path distance) is equal to the displacement derived from the effective feed rate EFR. This iterative process may include the path handler 82 repeatedly checking if the next segment's distance would exceed the EFR displacement, and if so, the path handler 82 interpolates linearly within that path segment PS to determine the precise location along the path segment PS where the EFR displacement is reached. This location becomes the origin of the next target pose TP. This iterative path interpolation process may also include smoothing filters on the interpolated path points, either time domain or spatial, acceleration filters, etc., before setting the result as the origin of the next target pose TP.

The target pose TP may then sent to the path constraint calculator 84 to compute three virtual constraints. In this example, these virtual constraints include x, y, z virtual constraints to be applied to effectively move the tool 20 from the current commanded pose CP of the tool 20 to the target pose TP (more or less constraints are also possible). These three constraints are computed based on the difference between the current commanded pose and the target pose TP. Of course, in other versions, orientation constraints could also be defined based on differences between current orientations and desired orientations. The three virtual constraints defined by the path constraint calculator 84 are then input into the constraint solver 86 (possibly with boundary constraints and/or other constraints, as shown in FIG. 10) to be processed by the constraint solver 86 to determine a resulting constraint force $F_c$. The virtual simulator 88 then conducts the virtual simulation 88 to ultimately determine a next commanded pose CP. The constraint solver 86 calculates the constraint force $F_c$ to be virtually applied to the tool 20 in the virtual simulator 88 based on the three virtual constraints (x, y, z) which act to effectively cancel out components of user forces at the TCP normal and tangential to the tool path TP (which may otherwise cause the TCP of the tool 20 to move relative to the path TP). The constraint force $F_c$ constrains movement of the TCP of the tool 20 at the next commanded pose CP, until the next iteration is immediately executed. In effect, the constraint force $F_c$ limits the hybrid mode control so that the tool 20 remains on the tool path TP.

The virtual simulator 88 may consider the effects of other forces/constraints beyond the x, y, z constraints. For example, additional constraints could be utilized so that the target pose is also encoded with a desired orientation in one or more of the rotational degrees of freedom. In that case, one or more of the axes for the target pose TP could be chosen to give the desired orientation of the TCP coordinate frame (for that point on the tool path TP). Accordingly, more than three virtual constraints would be computed by the path constraint calculator 84 for both the position and orientation components. Thus, the hybrid mode may assist users in guiding the TCP of the tool 20 along the tool path TP, while also guiding the orientation of the tool 20 in one or more degrees of freedom. Path-defined orientations could be computed/determined by the path generator 68, either offline or during the procedure, based on the surgical approach, clinical access, etc., and passed into the path handler 82 as part of the tool path TP, such that the orientation of the tool 20 automatically changes in a desirable/predefined way as the TCP of the tool 20 automatically advances along the tool path TP. Alternatively, or additionally, a set of orientation constraints could be determined independently of the path constraint calculator 84 and passed into the constraint solver 86 as part of the 'other constraints' input. One example for this approach would be to have a 2-DOF set of orientation constraints (e.g., for a spherical bur) to keep the bur shaft within a predefined virtual aperture, as described in U.S. Pat. No. 9,566,122, hereby incorporated herein by reference. Other options for orientation control are possible, such as no orientation control whereby the user can freely reorient the tool 20. Thus, two or three virtual constraints for the TCP position could come from the path constraint calculator 84, and additional constraints could be provided by an independent orientation control source. The position and orientation constraints, or individual constraints, can have different stiffness/damping tuning to give a desired user interaction and feel. The constraint solver 86 solves the full set of constraints and outputs a commanded pose CP to the motion control 76.

The system further enables the user to reorient the tool 20 along the tool path TP without necessarily changing the effective or predetermined feed rate. To do so, the user may press a switch or trigger on the end effector or tool 20 as it is advanced along the tool path TP. As the switch or trigger is pressed, the user applies forces/torques to reorient the tool 20. Alternatively, the forces/torques may be applied without pressing the trigger/switch. The system can utilize components of force/torque from Fext that are off the tool path or non-tangential to the tool path in the virtual simulation to determine how to reorient the tool 20 while advancing the tool 20 along the path. Virtual constraints can be utilized to keep the tool 20 on the tool path during this reorientation. This reorientation technique may be beneficial to enable the user to ergonomically orient the tool as desired during advancement. Additionally, reorientation during advancement may be useful to avoid potential collisions between the tool shaft and the environment. Should the applied forces/torques be great enough or above a threshold, the system may determine that the user intends to pull the tool 20 off the tool path TP and may allow the same. This situation is described below.

The techniques described herein can utilize constraint equations and data, forward dynamics algorithms, rigid body calculations, constraint force calculations, and virtual simulations like those described in U.S Patent Application Publication No. US 2020/0281676 A1, entitled "Systems and Methods for Controlling Movement of a Surgical Tool Along a Predefined Path", the contents of which are hereby incorporated by reference in their entirety.

D. Example Hybrid Mode Rules

The path handler 82 and/or feed rate evaluator 87 may implement different rules or conditions limiting the hybrid control mode. The following rules are provided only as examples and need not limit the scope of the disclosure. The rules may or may not be applied, depending on the situation.

Figures 12A, 12B:
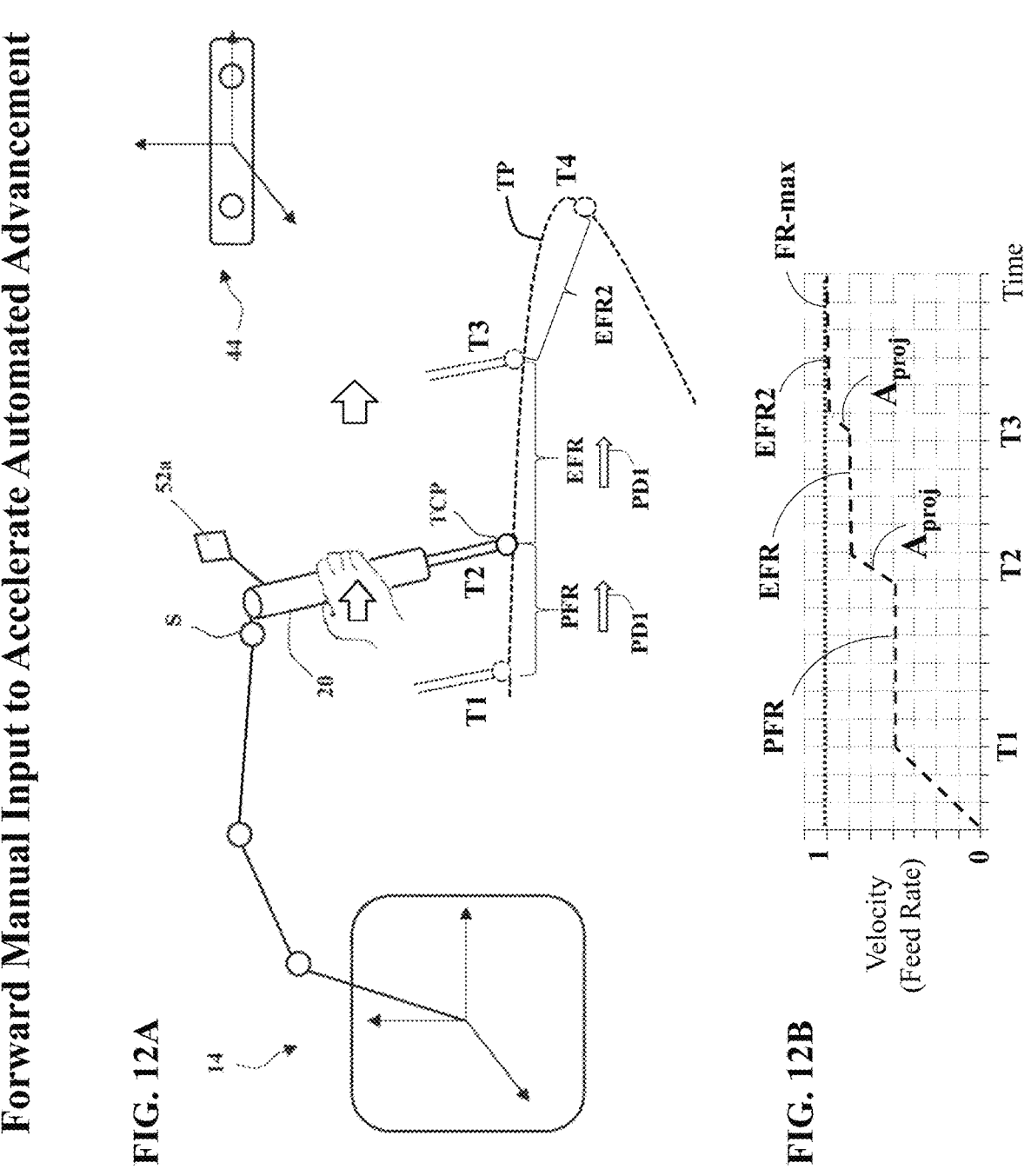
FIG. 12A is a simplified diagram of the robotic surgical system illustrating an example of the hybrid control mode wherein a forward manual input is applied to the tool by a user to accelerate automated advancement of the tool along the tool path.
FIG. 12B is a graph illustrating the respective feed rate of the tool for the various time steps corresponding to the example of FIG. 12A.

One rule that may be set is a maximum velocity, shown in the FIG. 12B as FR-max. The feed rate of the tool 20 in the hybrid mode may be limited so that the feed rate does not exceed the maximum velocity. The maximum velocity may be set to be greater than the predetermined feed rate PFR. Therefore, when the feed rate of the tool 20 is based on the predetermined feed rate PFR without Fext input, the maximum velocity will not be reached. Without the maximum velocity limit, the tool 20 could theoretically be moved at an unstable or unsafe speed in response to an excessive input force Fext. Therefore, the maximum velocity provides a speed limit on the user's manual intervention of automated advancement of the tool 20.

The path handler 82 and/or feed rate evaluator 87 may implement another rule to regulate velocity "ramp up" to avoid abrupt switching of the feed rate based on Fext and to provide smooth motion of the tool 20 in the hybrid mode. For example, certain initial feed rates, derived from the predetermined feed rate PFR, may have velocities (or default acceleration) to gradually increase the feed rate of the tool 20 until eventually a constant velocity is reached for automated advancement for the remaining portions of the tool path TP. Assuming no Fext is initially applied, the default setting is to smoothly ramp up the feed rate according to this default acceleration. However, if Fext is applied, it may be undesirable to enable the user to override this smooth transition by applying an excessive Fext. Therefore, in one example, the modules 82, 87 evaluate whether the effective feed rate EFR would be greater than certain initial feed rates by a predetermined threshold. The threshold may be one value for each relevant iteration, or the threshold may change for one or more iterations, i.e., depending on the velocity for the initial feed rate. If the condition is met, the modules 82, 87 may determine that the offset feed rate should not be added to the initial feed rate. In effect, this means that the applied force Fext would be temporarily disregarded to provide smooth tool motion during velocity ramp up. This rule may be applied for any velocity transition of the tool 20 and need not be limited to the initial portion of the tool path TP. For example, the velocity transition may occur after the tool 20 changes direction, is released, or is held in a stationary position by virtue of the externally applied forces Fext. If the threshold is not met, then the offset feed rate may be added to the initial feed rate to result in the velocity of the tool 20 accelerating at a faster rate than the default acceleration. In other examples, the effective feed rate EFR may be blended with the initial feed rates.

The path handler 82 and/or feed rate evaluator 87 may evaluate whether the feed rate of the tool 20 has exceeded predetermined feed rate PFR. If the predetermined feed rate PFR has not been exceeded, then the default acceleration can be applied to gradually increase the feed rate of the tool 20 until the predetermined feed rate PFR is reached. However, if the predetermined feed rate PFR has been exceeded, the path handler 82 and/or feed rate evaluator 87 may override the predetermined feed rate PFR with the effective feed rate EFR derived from Fext and the above calculations. In turn, this control enables the user to manually set the feed rate of the tool 20 above the predetermined feed rate PFR. Should the effective feed rate EFR drop below the predetermined feed rate PFR, then the system may reinstate the predetermined feed rate or may maintain the EFR, depending on the user's intentions, detected conditions, and/or user defined settings.

E. Hybrid Mode Examples

FIGS. 11-18 illustrate various examples of how the above-described computation can be implemented to move the tool 20 in the hybrid mode. Some of these examples involve manually applied forces/torques to the sensor S, while other examples do not. For each example, an illustration of the tool 20 along the path TP is shown for various time steps. Accompanying each illustration is a chart showing the velocity or feed rate of the tool 20 for the specific example shown. The manipulator 14, navigation system 32, and tool 20 are shown in a simplified form for ease of illustration. Any of the examples of FIGS. 11-18 may be utilized in the hybrid mode, individually, or as a combination of actions. The hybrid mode may perform actions beyond those shown in FIGS. 11-18.

1. Automated Advancement (No Manual Input)

Figures 11A, 11B:
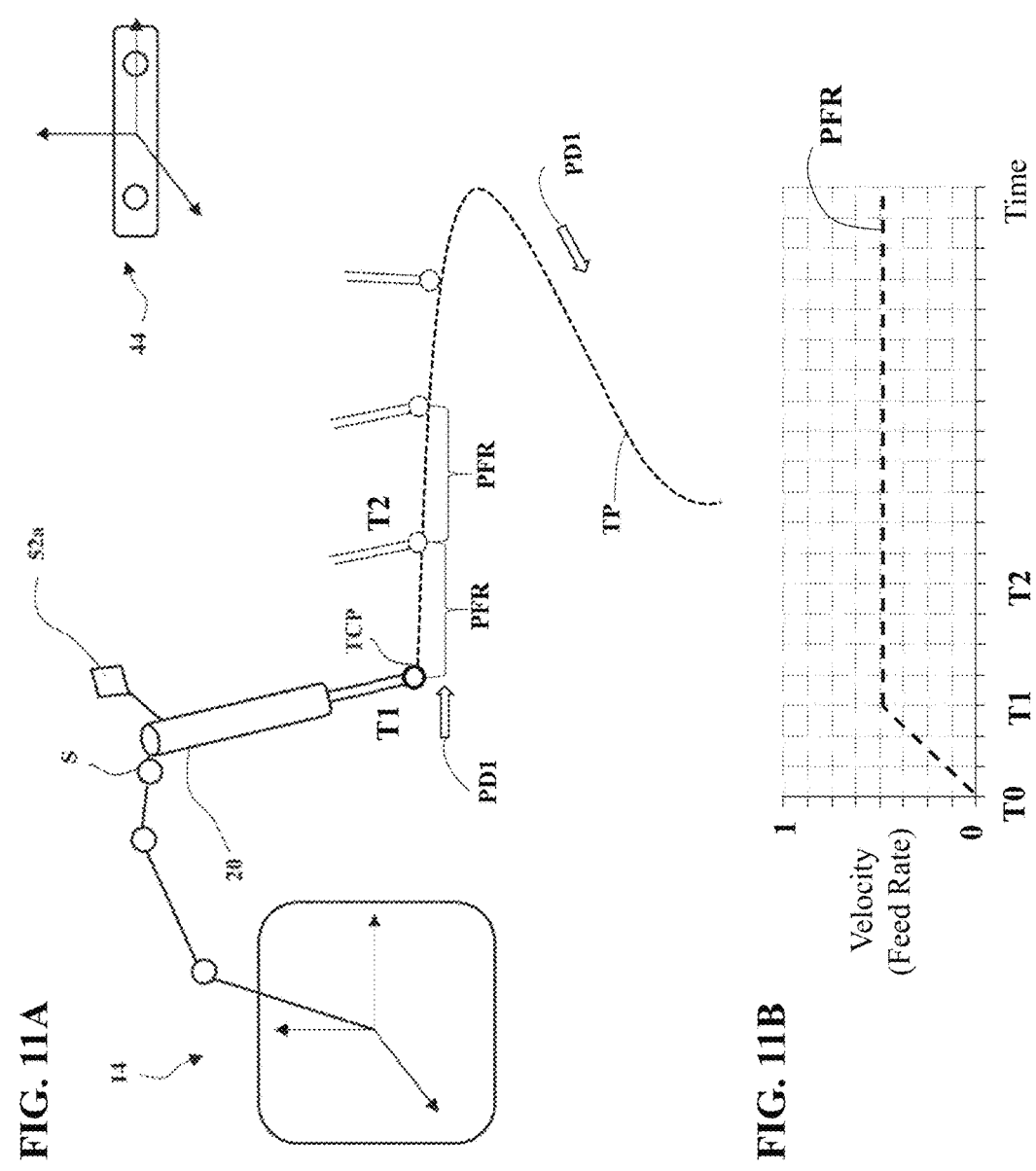
FIG. 11A is a simplified diagram of the robotic surgical system illustrating an example of automated advancement of the tool along the tool path, wherein no manual force is applied to the tool during advancement.
FIG. 11B is a graph illustrating the respective feed rate of the tool for the various time steps corresponding to the example of FIG. 11A.

Starting with FIGS. 11A and 11B, a situation is illustrated wherein the tool 20 is automatically advanced along the tool path TP in the hybrid mode, but without any current input from the force/torque sensor S. In accordance with the hybrid mode, absent any external force Fext, the tool 20 will proceed along the tool path TP automatically according to the predetermined feed rate PFR. The terms "forward" and "reverse" to describe tool movement along the tool path TP are used in this description for simplicity in understanding. However, these relative terms may have different meaning depending on the perspective of the user, the tool, or the system. It is contemplated that automated advancement, as described throughout, may be implemented to advance the tool in the forward or the reverse direction, as the default setting.

This example assumes the tool 20 was initially at rest at T0. Hence, the chart in FIG. 11B illustrates the feed rate to be 0. After T0, the feed rate is gradually increased tool 20 by the default acceleration until the predetermined feed rate PFR is reached at T1. The tool path direction is represented by PD1, a default forward direction. Once the predetermined feed rate PFR is reached, the predetermined feed rate PFR is applied for each subsequent path segment. In this example, PFR is a constant velocity. However, as described, the PFR need not be constant throughout the tool path TP. For example, the PFR could be defined to ramp down the velocity before the end point EP is reached. As described above, the automated advancement can guide the tool 20 according to the PFR until the end point is reached. Alternatively, automated advancement can continuously move the tool 20 indefinitely along a closed path (loop) according to PFR until some terminating event is identified to stop movement. Although, this example illustrates the automated mode aspect of the hybrid mode, it does not include input from the force/torque sensor S. Though this example is important to understand automated advancement, it is only a partial representation of the hybrid mode. The remaining examples illustrate situations in which automated advancement is combined with input from the force/torque sensor S.

2. Forward Manual Input to Accelerate Automated Advancement

FIGS. 12A and 12B illustrate a situation in which the user applies a forward external forces/torque to the force/torque sensor S during automated advancement of the tool 20 along the tool path TP. In other words, the applied force Fext has components in the same direction as the automated path direction PD1 of the tool 20. Thus, the user manually augments or accelerates the rate of automated advancement. In this situation, the effective feed rate EFR is computed, as described above, based on Fext as an input. The effective feed rate EFR is greater than the predetermined feed rate PFR based on the user applied force. In this case, the user applied force is applied only after the tool 20 is moved according to the predetermined feed rate PFR. At TO the tool is at rest and at T1 the tool 20 reaches the predetermined feed rate PFR. At T2, the user forward manual input is applied to the tool 20 and the acceleration projection (Aproj) is computed based on the Fext, which the control system 60 uses to determine EFR. In effect, application of the acceleration projection (Aproj) results in a change in velocity of PFR to reach EFR. The speed of the tool 20 proceeds at the effective feed rate EFR between T2 and T3. At T3, a second user forward manual input is applied to the tool 20. In this example, the second manual input is more forceful than the first input. Thus, another iteration of Fext is processed as input and a second acceleration projection (Aproj) is computed based on the Fext, which the control system 60 uses to determine a second effective feed rate EFR2. Application of the second acceleration projection (Aproj) results in another change in velocity of EFR to reach EFR2. The speed of the tool 20 proceeds with the second effective feed rate EFR2 after T3. In this example, the control system 60 further implements the maximum velocity limit FR-max to limit the second effective feed rate EFR2. In other words, the second effective feed rate EFR2 is limited so that the speed does not exceed the maximum velocity.

The acceleration of the automated advancement feed rate in this manner can be beneficial for many practical reasons. For example, the user may desire to move the tool 20 to the end point EP more quickly than the default rate can provide. This could reduce time in the operating room. In other instances, the user may accelerate automated advancement to evade potential collisions with the tool 20.

3. Forward Manual Input Release Along Forward Path Direction

Figures 13A, 13B:
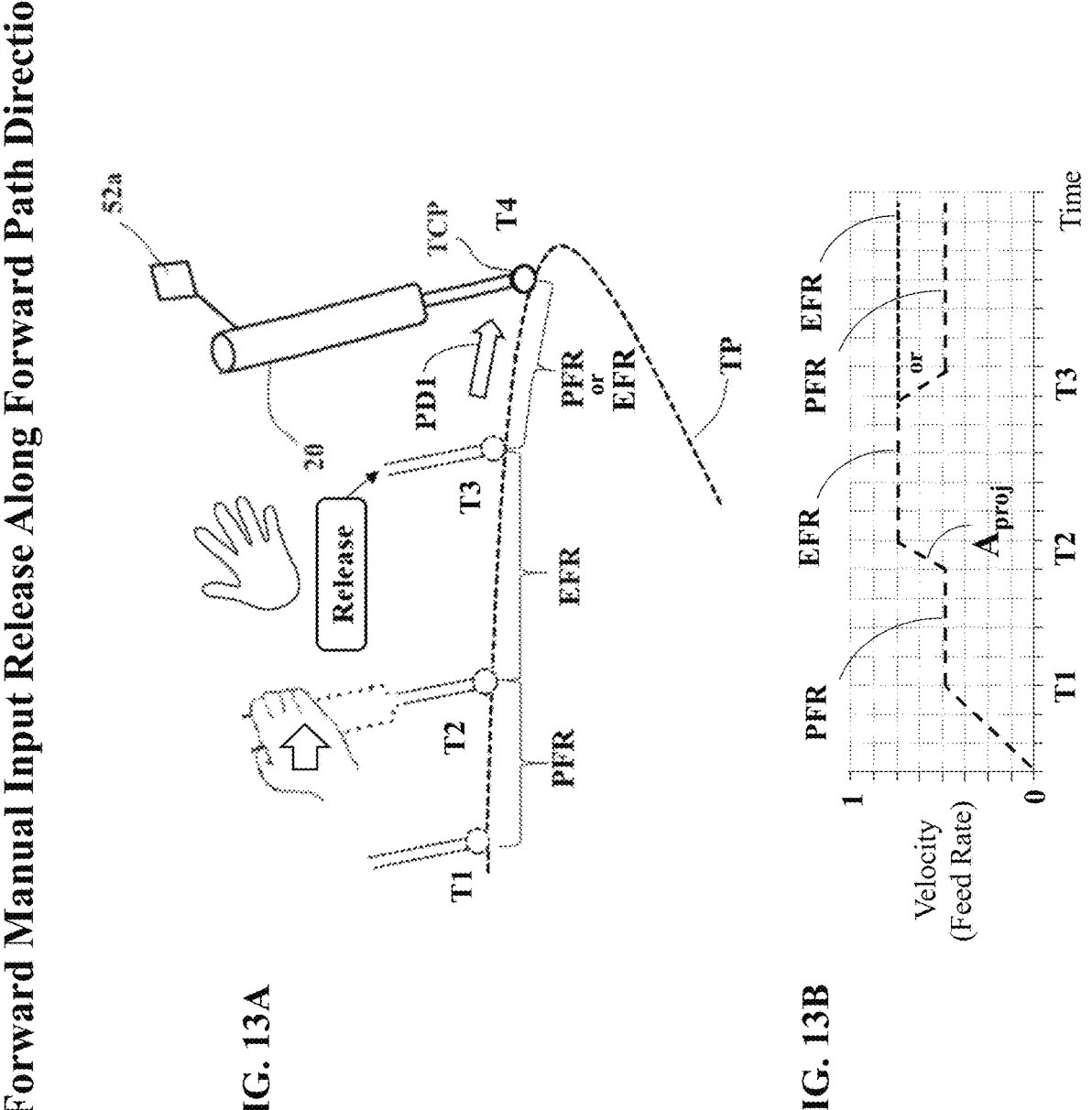
FIG. 13A is a simplified diagram of the robotic surgical system illustrating an example of the hybrid control mode wherein the user applies forward manual input to move the tool in a forward direction, then the user releases the forward manual input to reinstate automated advancement of the tool along the tool path in the forward direction.
FIG. 13B is a graph illustrating the respective feed rate of the tool for the various time steps corresponding to the example of FIG. 13A.

FIGS. 13A and 13B illustrate a situation in which the user applies a forward external forces/torque during automated advancement of the tool 20, and thereafter the user releases the tool 20 such that Fext is no longer applied. This example exemplifies how the hybrid mode provides automated advancement as a default control. At T1, the tool 20 automatically reaches the predetermined feed rate PFR without user input. At T2, the user applies forward manual input to the tool 20 such that Fext has components in the same direction as the path direction PD1 of the tool 20. The effective feed rate EFR is computed based on Fext as an input and is greater than the predetermined feed rate PFR. Thus, the user temporarily accelerates the rate of automated advancement. The speed of the tool 20 proceeds with the effective feed rate EFR between T2 and T3. The user then releases the tool at T3 such that Fext is reduced to zero input value. The path handler modules 82, 87 may identify the condition of Fext being zero or unavailable.

In response to detection of the tool 20 being released, the path handler modules 82, 87 may output one of two different responses for the next time step, T3. One response is to restore the predetermined feed rate PFR and another response is to maintain the effective feed rate EFR. In one example, as shown in FIG. 13B, the previous predetermined feed rate PFR that was implemented prior to application of Fext is restored. Here, in response to the user releasing the tool 20, the feed rate will decelerate to the PFR because the PFR was slower than the last EFR. However, the predetermined feed rate PFR which is restored may or may not be the PFR implemented before the manual input. The path handler modules 82, 87 can apply a default or predetermined deceleration to provide a smooth transition from EFR to PFR at T3. The path handler modules 82, 87 may compute the deceleration value by computing the change in velocity between EFR to PFR over change in time. Alternatively, the path handler modules 82, 87 can obtain the value of the deceleration based on a look-up table which provides various default deceleration values for respective velocity differences (e.g., EFR–PFR). So long as the user does not apply any manual force to the tool 20 after T3, the tool 20 will continue to automatically advance along the tool path TP according to the PFR until a condition or end point EP stops the tool 20.

As shown in FIG. 13B, the second response is to continue to advance the tool 20 according to the last effective feed rate EFR (without Fext being applied), where the EFR is the feed rate that was implemented in the previous time step (e.g., T2). Here, in response to the user releasing the tool 20, the feed rate will be maintained at the EFR, which was effectively set by the user applying Fext. So long as the user does not apply any manual force to the tool 20 after T3, the tool 20 will continue to automatically advance along the tool path TP according to the EFR until a condition or end point EP stops the tool 20.

As will be described below, the release and restore example of FIG. 13 could alternatively be implemented in response to a negative Fext applied by the user against the predetermined path direction PD1 (as shown in FIG. 16, for example).

The manual releasing of applied force and restoration of the automated advancement feed rate in this manner can be beneficial for many practical reasons. The user may desire to move the tool 20 more quickly or more slowly for a temporary period before resuming automated movement. For example, the user may temporarily decelerate the feed rate because an object is obstructing the tool path TP. Once the object is removed from the path TP, the user releases and restores automated advancement. In another example, the user may apply force to temporarily accelerate the feed rate to quickly evade an impending obstruction, and thereafter release and restore automated advancement. In another example, the user may desire to temporarily apply force to accelerate the feed rate to traverse a portion of the tool path TP that the user considers to be tedious or distant from the anatomy. In another example, the user may temporarily decelerate the feed rate to intentionally cause a delay for some surgical purpose. For instance, the saw may be advanced along the tool path TP towards the cut plane CPL. In the process, the user may realize that a surgical component, such as a cut guide, retractor, or irrigation tool, may need adjustment or installation near the surgical site. To provide time for making such adjustments, the user may temporarily decelerate the tool and then release once such adjustments are complete.

4. Reverse Manual Input to Decelerate Forward Automated Advancement

Figures 14A, 14B:
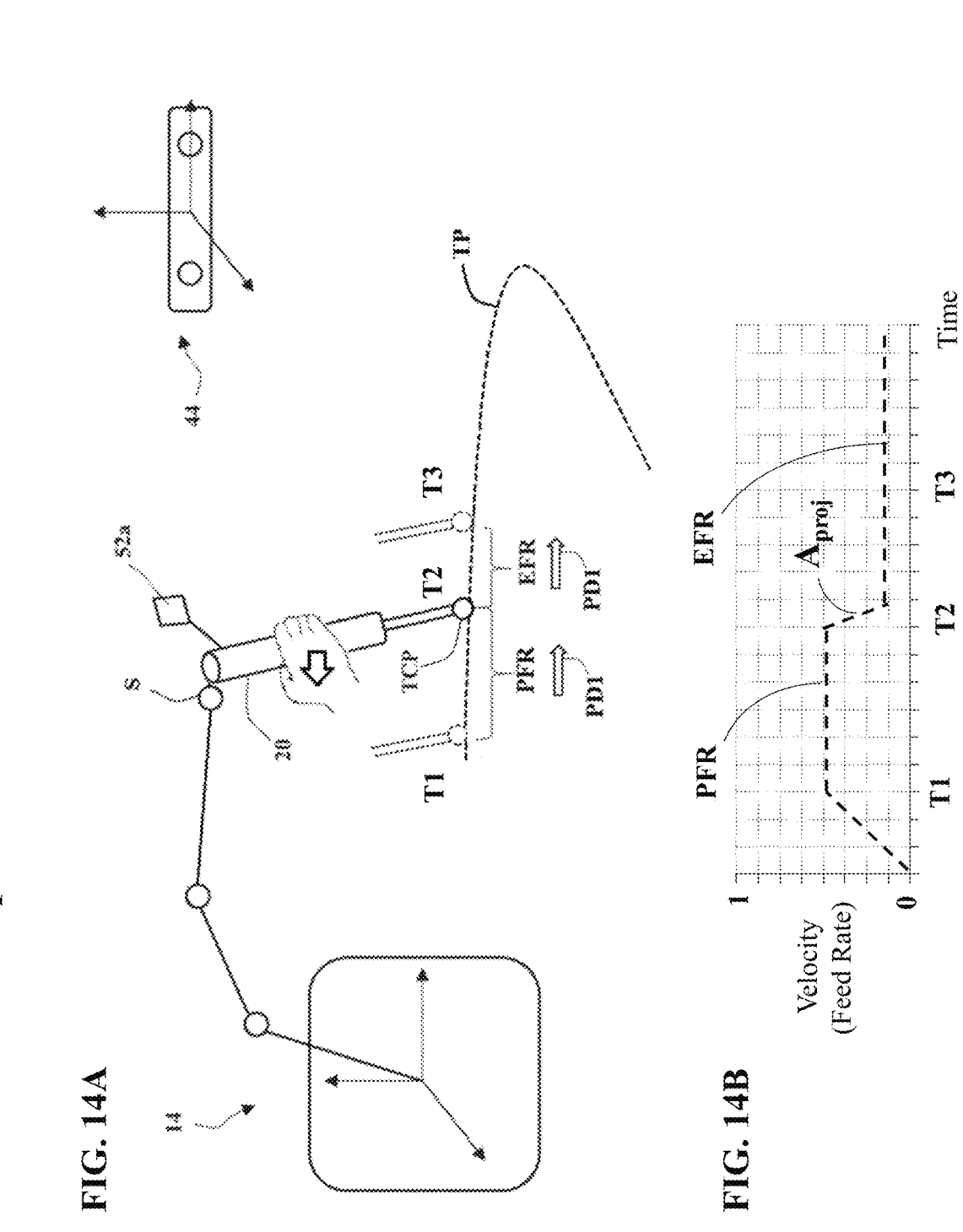
FIG. 14A is a simplified diagram of the robotic surgical system illustrating an example of the hybrid control mode wherein a reverse manual input is applied to the tool by the user to decelerate forward automated advancement of the tool along the tool.
FIG. 14B is a graph illustrating the respective feed rate of the tool for the various time steps corresponding to the example of FIG. 14A.

FIGS. 14A and 14B illustrate a situation in which the user applies a reverse external forces/torque to the force/torque sensor S during automated advancement of the tool 20 along the tool path TP. In other words, the applied force Fext has components in the opposite direction as the automated path direction PD1 of the tool 20. Thus, the user effectively decelerates the rate of automated advancement. In one sense, this example may be understood as impeding or resisting automated advancement, while still allowing the original direction of advancement. During this process, the user will haptically feel the resistance to the default forward advancement. The effective feed rate EFR is computed based on a negative Fext as an input and the effective feed rate EFR is less than the predetermined feed rate PFR but still positive. At T1, the tool 20 reaches the predetermined feed rate PFR during automated advancement and at T2, the user gently applies force by pulling the tool 20 against the path direction PD1. At T2, a negative acceleration projection (Aproj) is computed based on the negative Fext, which is utilized to compute a negative offset feed rate to reduce the velocity from PFR to EFR. However, the negative offset feed rate does not completely offset the initial feed rate. Hence, while the negative Fext is applied, the tool 20 will move in the same path direction PD1, but at a slower feed rate.

The deceleration of the automated advancement feed rate in this manner can provides many benefits to the user experience. For example, the user may desire to move the tool 20 to the end point EP more slowly than the default rate. Deceleration may also give comfort to certain users who desire to feel the tool 20 before relinquishing control to automated advancement. In other instances, the user may decelerate automated advancement to evade potential collisions with the tool 20 or to slow the tool 20 to intentionally delay, pending removal of an undesirable condition or completion of a surgical adjustment near the end point EP.

5. Reverse Manual Input to Override Forward Automated Advancement

Figures 15A, 15B:
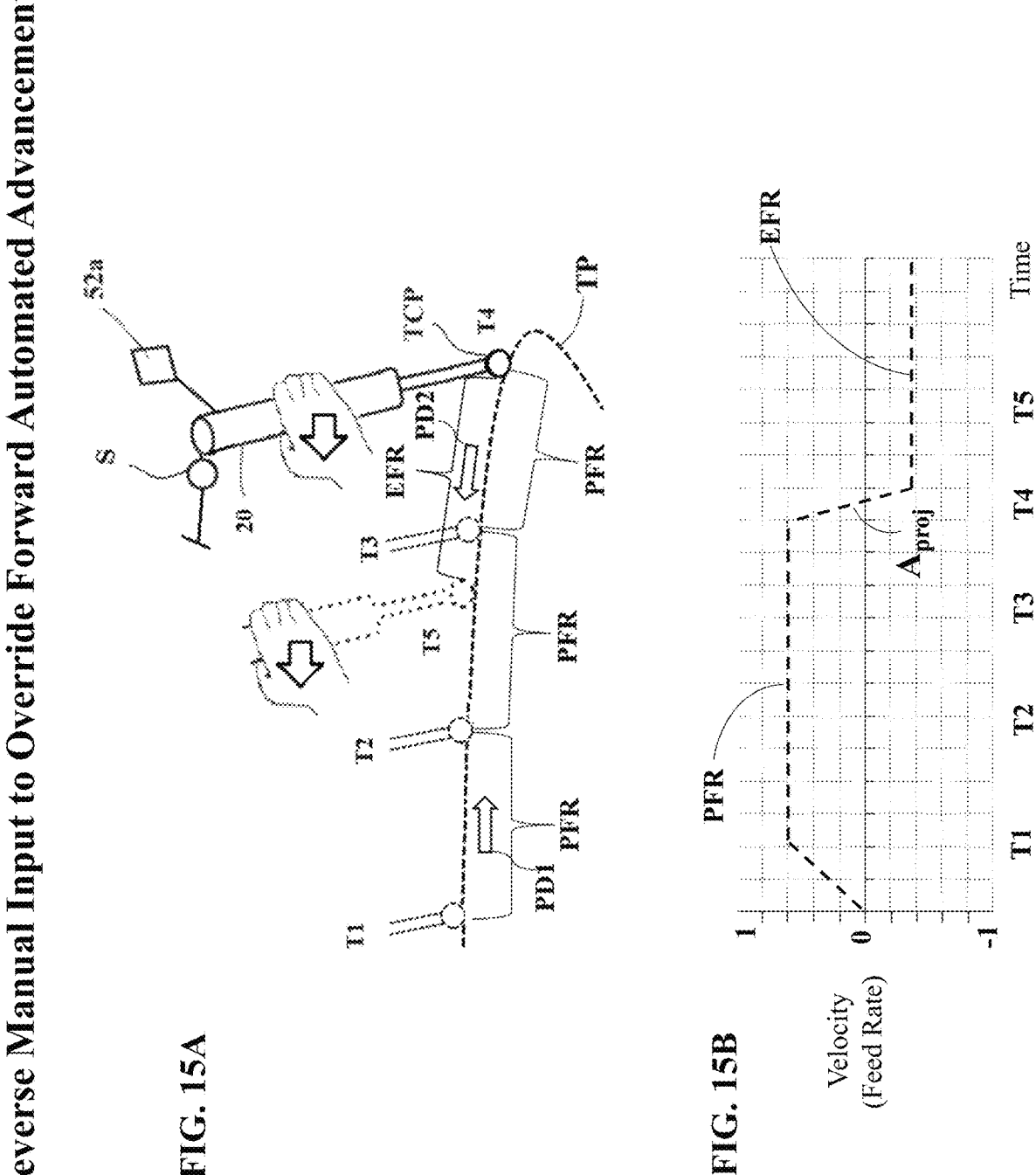
FIG. 15A is a simplified diagram of the robotic surgical system illustrating an example of the hybrid control mode wherein a reverse manual input is applied to the tool by the user to temporarily override automated advancement and move the tool in an opposite direction along the tool path.
FIG. 15B is a graph illustrating the respective feed rate of the tool for the various time steps corresponding to the example of FIG. 15A.

FIGS. 15A and 15B illustrate a situation, like that of FIG. 14, in which the user applies a reverse external forces/torque to the force/torque sensor S during automated advancement of the tool 20 along the tool path TP. In other words, the applied force Fext has components in the opposite direction as the automated path direction PD1 of the tool 20. However, in this example, the magnitude of Fext is sufficient to overcome or override the automated advancement. In other words, the user applies a manual force sufficient to reverse the direction of the tool 20 along the path. During this process, the user will haptically feel resistance to the default forward advancement. In this example, at T1, the tool 20 reaches the predetermined feed rate PFR during automated advancement and continues at the PFR until T4, at which the user applies force by pulling the tool 20 against the predetermined path direction PD1. In so doing, the user effectively decreases the rate of automated advancement to 0 and a negative feed rate is immediately implemented (in the reverse direction) based on the Fext. A negative acceleration projection (Aproj) is computed based on the negative Fext, which is utilized to compute a negative offset feed rate to reduce the velocity from PFR to EFR. Here, the negative offset feed rate completely offsets the initial feed rate. In the example shown, the EFR is negative and has a speed (absolute value) less than the predetermined feed rate PFR. Alternatively, the negative effective feed rate EFR may have a speed which could be equal to or greater than the predetermined feed rate PFR. Hence, while the negative Fext is applied, the tool 20 will move in the opposite or effective path direction PD2 according to the EFR.

The reversal and overriding of the automated advancement also provide many benefits to the user experience. For example, the user may desire to move the tool 20 along a portion of the tool path TP that was previously traversed. This may be done, for example, during manipulator 14 registration, to enable the navigation system 32 to recapture tracking data that may have been missed or lost. In another example, the direction may be reversed to provide room or delay for some surgical purpose. For instance, the saw may be advanced along the tool path TP towards the cut plane CPL. In the process, the user may realize that a surgical component, such as a cut guide, retractor, or irrigation tool, may need adjustment or installation near the surgical site. To avoid injury from the saw or to provide room for such adjustments, the user may apply force to reverse the tool direction. Direction reversal may also be utilized to evade potential collisions with the tool 20.

6. Reverse Manual Input Release Along Reverse Path Direction

Figures 16A, 16B:
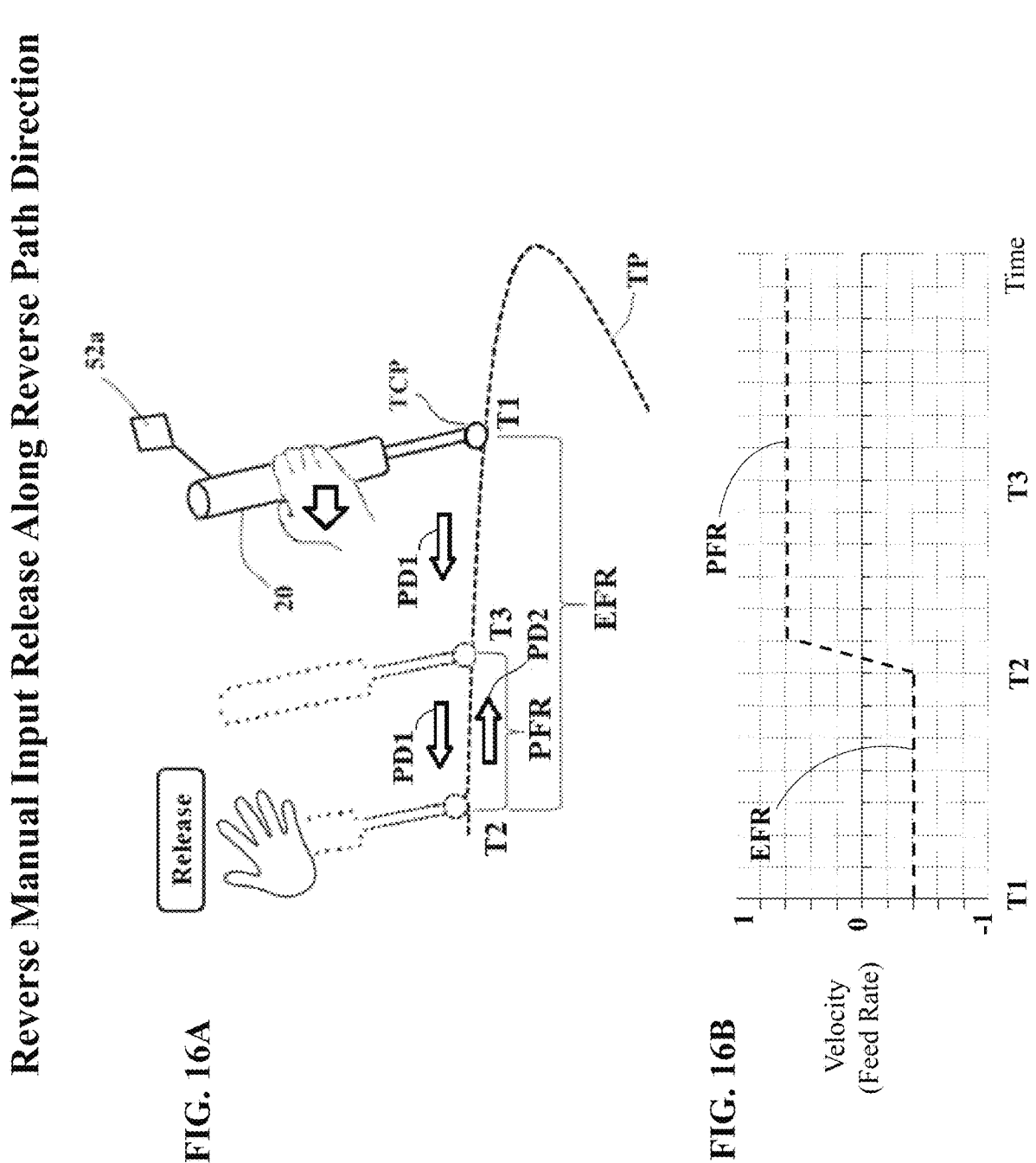
FIG. 16A is a simplified diagram of the robotic surgical system illustrating an example of the hybrid control mode wherein the user applies reverse manual input to move the tool in a reverse direction, then the user releases the reverse manual input to reinstate automated advancement of the tool along the tool path in a forward direction.
FIG. 16B is a graph illustrating the respective feed rate of the tool for the various time steps corresponding to the example of FIG. 16A.

FIGS. 16A and 16B illustrate a situation in which the user applies a reverse external forces/torque of the tool 20, and thereafter the user releases the tool 20 such that Fext is no longer applied. This example provides another instance of how the hybrid mode provides automated advancement as a default control. Before T1, the tool 20 may have been stationary or may have been advanced in the forward direction pursuant to the predetermined feed rate PFR. At T1, the user applies reverse manual input to the tool 20 such that Fext has components in the reverse path direction PD1 of the tool 20. After T1, the effective feed rate EFR is computed based on Fext as an input. In this example, it is assumed that the Fext is applied in a consistent manner During this period between T1 and T2, the user may feel resistance on the tool 20 as the tool 20 is moved reverse because the predetermined feed rate PFR will want to advance the tool 20 in the forward direction (PD2). Based on the user's input, the tool 20 proceeds with the effective feed rate EFR between T1 and T2. The user then releases the tool at T2 such that Fext is reduced to zero input value. The path handler modules 82, 87 may identify the condition of Fext being zero or unavailable.

In response to detection of the tool 20 being released at T2, the path handler modules 82, 87 may output a response to restore or initiate the predetermined feed rate PFR. The predetermined feed rate PFR may be initiated here for the first time or the PFR may be restored based on a prior implemented PFR applied at some time prior to T1. Here, in response to the user releasing the tool 20 at T2, the feed rate will accelerate to the PFR because the PFR is greater than the EFR. Pursuant to this acceleration, the path direction will then change from the reverse direction PD1 to the forward direction PD2.

The path handler modules 82, 87 can apply a default or predetermined acceleration to provide a smooth transition from EFR to PFR at T2. The path handler modules 82, 87 may compute the acceleration value by computing the change in velocity between EFR to PFR over change in time. Alternatively, the path handler modules 82, 87 can obtain the value of the acceleration based on a look-up table which provides various default acceleration values for respective velocity differences (e.g., PFR–EFR). So long as the user does not apply any manual force to the tool 20 after T2, the tool 20 will continue to automatically advance along the tool path TP at, and after T3, according to the PFR until a condition or end point EP stops the tool 20.

Another possibility is that after release of the tool 20 at T2 the tool 20 can continue to automatically advance according to the last effective feed rate EFR (without Fext being applied), where the EFR is the feed rate that was implemented at some prior time step. For example, in response to the user releasing the tool 20, the feed rate could be set at a positive value of the reverse EFR, which was effectively set by the user applying Fext.

The pulling back and manual releasing of applied force and restoration of the automated advancement feed rate in this manner can be beneficial for many practical reasons. The user may desire to pull the tool 20 back for a temporary period before resuming or initiating automated movement. For example, the user may desire to move the tool 20 away from an object obstructing the tool path TP. Once the object is removed from the path TP, the user releases and restores automated advancement. In another example, the user may apply force to reverse the tool direction to quickly evade an impending obstruction, and thereafter release and restore automated advancement. In another example, the user may desire to "feel" the path or resistive force before resuming automated advancement to provide the user with confidence of the guidance provided by the system. In another example, the user may temporarily pull back and manual release the tool 20 to intentionally to make room, or cause a delay, for some surgical purpose. For instance, the saw may be advanced along the tool path TP towards the cut plane CPL. In the process, the user may realize that a surgical component, such as a cut guide, retractor, or irrigation tool, may need adjustment or installation near the surgical site. To avoid injury from the saw or to provide room for such adjustments, the user may apply force to reverse the tool direction. In another example, the user may desire to pull back the tool 20 along a portion of the tool path TP that was previously traversed. This may be done, for example, during manipulator 14 registration, to enable the navigation system 32 to recapture tracking data that may have been missed or lost.

7. Reverse Manual Input to Offset Forward Automated Advancement

Figures 17A, 17B:
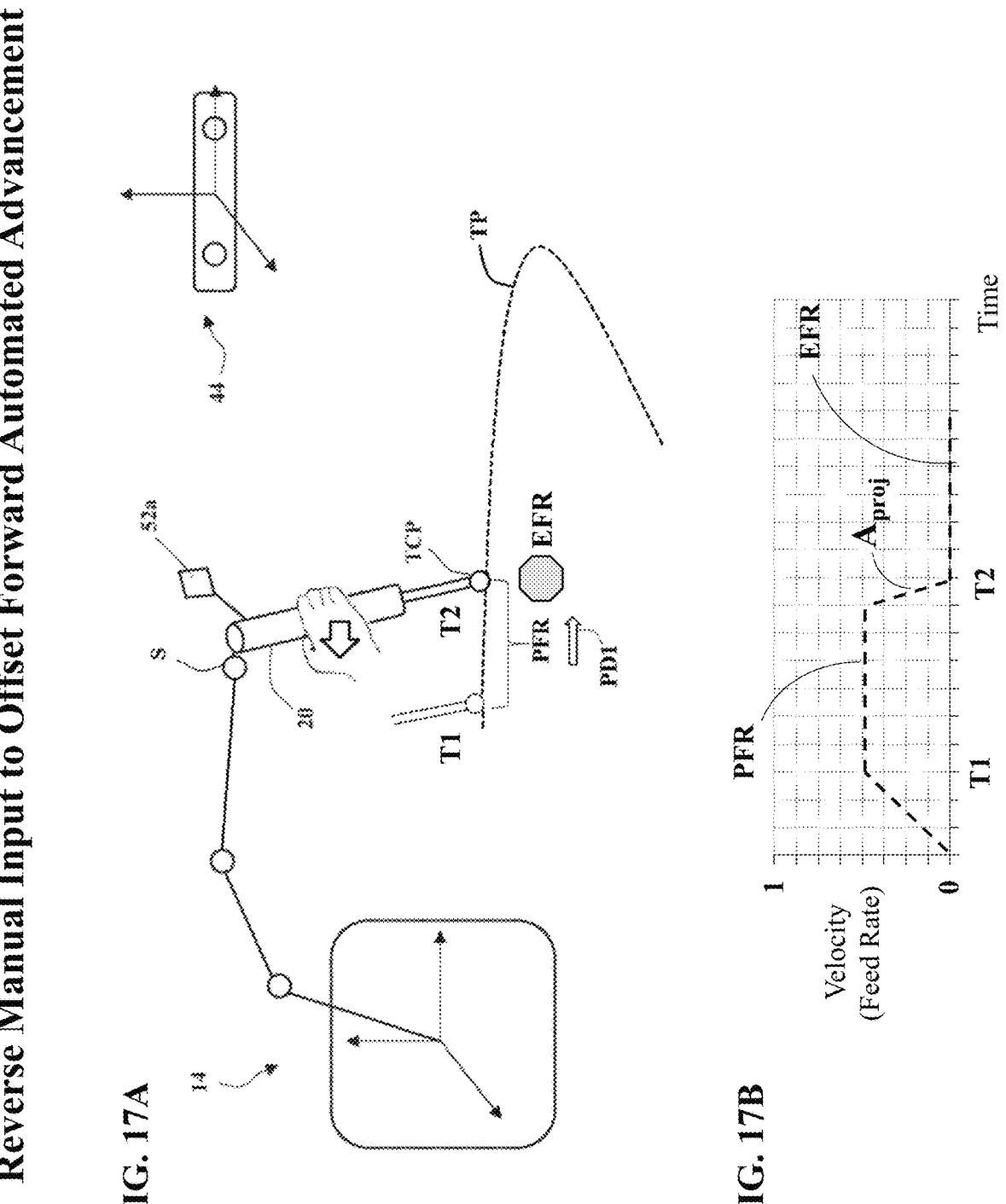
FIG. 17A is a simplified diagram of the robotic surgical system illustrating an example of the hybrid control mode wherein a reverse manual input is applied to the tool by the user to temporarily offset automated advancement of the tool such that the tool remains substantially stationary on the tool path.
FIG. 17B is a graph illustrating the respective feed rate of the tool for the various time steps corresponding to the example of FIG. 17A.

FIGS. 17A and 17B illustrate a situation, like that of FIG. 15, in which the user applies a reverse external forces/torque to the force/torque sensor S during automated advancement of the tool 20 along the tool path TP. In other words, the applied force Fext has components in the opposite direction as the automated path direction PD1 of the tool 20. However, in this example, the components of Fext are just enough to offset automated advancement. In other words, the user applies a manual force against the automated advancement sufficient to hold the tool 20 stationary on the tool 20, e.g., negating tool direction. In this example, at T1, the tool 20 reaches the predetermined feed rate PFR during automated advancement and continues at the PFR until T2, at which the user applies force by pulling the tool 20 against the predetermined path direction PD1. In so doing, the user manually decelerates the rate of automated advancement to 0. However, because Fext is just enough to offset the automated advancement, there is no negative feed rate immediately implemented (in the reverse direction). A negative acceleration projection (Aproj) is computed based on the negative Fext, which is utilized to compute a negative offset feed rate to reduce the velocity of PFR to a zero effective feed rate EFR. Here, the negative offset feed rate exactly offsets the initial feed rate. Hence, while the negative Fext is applied, the tool 20 will remain stationary on the tool path TP. Of course, if the negative offset feed rate offsets and exceeds the initial feed rate, it is possible that the tool 20 could temporarily change direction and move reverse along the tool path TP.

In practice, it may be challenging to hold the tool 20 stationary in this manner due to the precision required in continually applying an exact value of Fext for each time step. Hence, as iterations are quickly processed, the tool 20 may vibrate back and forth along the stationary position as each iteration of Fext is evaluated relative to the initial feed rate. To avoid such vibrations, the control system 60 or path handler modules 82, 87 could detect presence of the zero effective feed rate EFR for a threshold number of iterations (e.g., more than 10 iterations). If the threshold is met, the system can temporarily pause hybrid mode control or temporarily halt automated advancement. User confirmation may then be provided via a user interface to restart the hybrid mode. This temporary pausing and confirmation may be beneficial because, as a safeguard, the control system 60 can infer that the user has identified an issue causing the user to hold the tool 20 stationary and resist automated advancement. In other examples, if the threshold is met, the control system 60 can reverse the direction of the tool 20 along the path TP until a predetermined safety distance from the 'hold point' is reached.

8. Object Collision to Offset Forward Automated Advancement

Figures 18A, 18B:
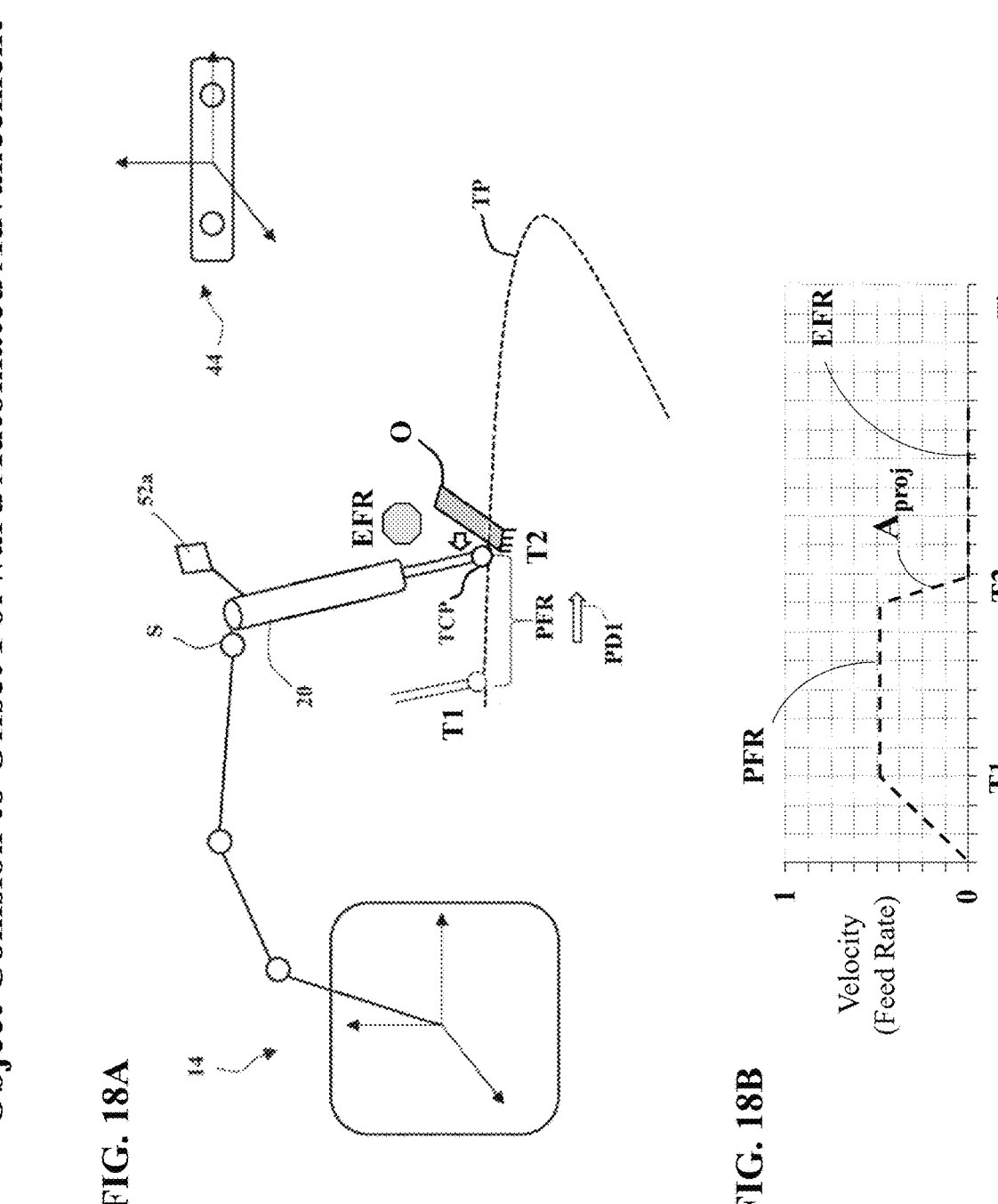
FIG. 18A is a simplified diagram of the robotic surgical system illustrating an example of the hybrid control mode wherein an external is applied to the tool by collision with an object to temporarily offset automated advancement of the tool such that the tool remains substantially stationary on the tool path.
FIG. 18B is a graph illustrating the respective feed rate of the tool for the various time steps corresponding to the example of FIG. 18A.

FIGS. 18A and 18B illustrate a situation in which the hybrid mode may respond to a collision between the tool 20 and an object (0) on the tool path TP that interferes with automated advancement of the tool 20. The object (0) in this example is assumed to be a stationary object and can be any surgical or non-surgical object, such as another tool (e.g., cut guide, retractor, tracker, or irrigation tool), the anatomy (e.g., bone, incision opening, etc.), or the like. In this example, an external force Fext is applied to the tool 20 and provided as an input by the force/torque sensor S. However, in this example, Fext is not provided by the user's manual force. Instead, Fext is provided through the object's (O) collision with the tool 20. The collision causes a negative Fext having components in the opposite direction as the automated path direction PD1 of the tool 20. Just as with the example of FIG. 17, in this example, the components of Fext are just enough to offset automated advancement. In other words, the collision causes a force against the automated advancement sufficient to hold the tool 20 stationary on the tool 20, e.g., negating tool direction. In this example, at T1, the tool 20 reaches the predetermined feed rate PFR during automated advancement and continues at the PFR until T2, at which the collision force pushes the tool 20 against the predetermined path direction PD1. In so doing, the collision decreases the rate of automated advancement to 0. However, because Fext is just enough to offset the automated advancement, there is no negative feed rate immediately implemented (in the reverse direction). A negative acceleration projection (Aproj) is computed based on the negative Fext, which is utilized to compute a negative offset feed rate to reduce the velocity of PFR to a zero effective feed rate EFR. Here, the negative offset feed rate exactly offsets the initial feed rate. Hence, so long as the object (O) impedes the tool path TP and assuming the object (O) does not move, the tool 20 will remain stationary on the tool path TP. In some instances, the negative offset feed rate may offset and exceed the initial feed rate causing the tool 20 reverse direction along the tool path TP.

In practice, it may be challenging to hold the tool 20 stationary against the object (O) due to the precision required in continually applying an exact value of Fext for each time step. Hence, as iterations are quickly processed, the tool 20 may vibrate back and forth along the stationary position as each iteration of Fext is evaluated relative to the initial feed rate. To avoid such vibrations, the control system 60 or path handler modules 82, 87 could detect presence of the zero effective feed rate EFR for a threshold number of iterations (e.g., more than 10 iterations). If the threshold is met, the system can temporarily pause hybrid mode control or temporarily halt automated advancement. User confirmation may then be provided via a user interface to restart the hybrid mode. This temporary pausing and confirmation may be beneficial because, as a safeguard, the control system 60 can infer there may be a collision resisting advancement of the tool 20. In other examples, if the threshold is met, the control system 60 can reverse the direction of the tool 20 along the path TP until a predetermined safety distance from the collision point is reached.

9. Manual Input to Exit Hybrid Control Mode

During hybrid control advancement of the tool 20, a condition may occur that causes the surgeon to suddenly attempt to pull the tool 20 off the tool path TP. This situation may occur whether or not manual force input requires continual pressing of the trigger or switch on the tool 20 or end effector. Should this event occur, the force/torque sensor S is exposed to relatively high forces and torques in response to the practitioner's efforts to displace the tool 20 away from the tool path TP. A force overrider module, implemented by the behavior controller, can provide input into path handler 82 or feed rate evaluator 87 based on this event in response to the forces/torques exceeding a threshold or high force/torque limit governed by the force overrider. The magnitude and direction of the forces/torques can be evaluated by the force overrider to determine the extent to which the applied forces/torques deviate from the tool path TP. The force overrider module is configured to provide the input to transition the manipulator 14 from the hybrid control mode to the manual mode. This can result in the path handler 82 or feed rate evaluator 87 outputting a zero-speed feed rate and stopping the automated advancement of the tool 20. With the manual mode, the user then is free to control the tool 20 to exit the tool path TP. Alternatively, the user may maintain the tool 20 on the tool path TP in the manual mode. The user can reinstate the hybrid mode using any user interface UI or technique described above.

Several embodiments have been described in the foregoing description. However, the embodiments discussed herein are not intended to be exhaustive or limit the invention to any particular form. The terminology, which has been utilized, is intended to be in the nature of words of description rather than of limitation. Many modifications and variations are possible in light of the above teachings and the invention may be practiced otherwise than as specifically described.

What is claimed is:

1. A robotic surgical system comprising:
a surgical tool;
a manipulator configured to support the surgical tool, the manipulator comprising a plurality of links and joints;
a force/torque sensor configured to measure forces/torques applied to the surgical tool by a user; and
a control system configured to:
obtain a predetermined tool path for the surgical tool, the predetermined tool path comprising an end location;
command the manipulator to perform an automated advancement of the surgical tool along the predetermined tool path in a first path direction and according to a predetermined feed rate to guide the surgical tool to the end location;
during the automated advancement of the surgical tool, receive an input from the force/torque sensor in response to forces/torques applied to the surgical tool by the user;

evaluate an effect of the input from the force/torque sensor on the automated advancement of the surgical tool along the predetermined tool path in the first path direction and according to the predetermined feed rate;
based on evaluation of the effect, determine an effective feed rate and an effective path direction for the surgical tool with respect to the predetermined tool path; and
determine a commanded action for the manipulator and the surgical tool with respect to the predetermined tool path based on the effective feed rate and effective path direction.

2. The robotic surgical system of claim 1, wherein:
the effective feed rate is greater than the predetermined feed rate;
the effective path direction is the first path direction; and
the commanded action comprises automated advancement of the surgical tool along the predetermined tool path in the first path direction and according to the effective feed rate.

3. The robotic surgical system of claim 2, wherein automated advancement of the surgical tool according to the effective feed rate is based on a temporary input from the force/torque sensor and automated advancement of the surgical tool according to the effective feed rate is configured to continue absent input from the force/torque sensor.

4. The robotic surgical system of claim 1, wherein:
the effective feed rate is less than the predetermined feed rate;
the effective path direction is the first path direction; and
the commanded action comprises automated advancement of the surgical tool along the predetermined tool path in the first path direction and according to the effective feed rate or the predetermined feed rate.

5. The robotic surgical system of claim 1, wherein:
the effective path direction is a second path direction being opposite the first path direction; and
the commanded action comprises advancement of the surgical tool along the predetermined tool path in the second path direction and according to the effective feed rate.

6. The robotic surgical system of claim 5, wherein the commanded action further comprises simultaneously resisting advancement of the surgical tool in the second path direction by attempted automated advancement of the surgical tool in the first path direction.

7. The robotic surgical system of claim 1, wherein the control system is configured to:
detect absence of the input from the force/torque sensor; and
in response, command the manipulator to initiate or restore the automated advancement of the surgical tool along the predetermined tool path in the first path direction and according to the predetermined feed rate or according to a prior effective feed rate.

8. The robotic surgical system of claim 1, wherein the surgical tool is a saw, and the end location is configured to align the saw with a cutting plane associated with a target site.

9. The robotic surgical system of claim 1, wherein the surgical tool is configured to be activated to remove tissue, and wherein the control system is configured to deactivate the surgical tool during the automated advancement of the surgical tool along the predetermined tool path.

10. The robotic surgical system of claim 1, wherein the control system is configured to:

determine, based on the input from the force/torque sensor, a virtual acceleration vector; and evaluate an effect of the virtual acceleration vector on the automated advancement of the surgical tool to determine the effective feed rate and the effective path direction for the surgical tool with respect to the predetermined tool path.

11. The robotic surgical system of claim 10, wherein to determine the virtual acceleration vector, the control system is configured to:

model the surgical tool as a virtual rigid body comprising a virtual mass;

compute a force projection to the virtual rigid body based on the forces/torques applied to the surgical tool; and compute the virtual acceleration vector based on the force projection and the virtual mass.

12. The robotic surgical system of claim 11, wherein to determine the effective feed rate and the effective path direction for the surgical tool with respect to the predetermined tool path, the control system is configured to:

compute a tool path direction based on a segment of the predetermined tool path on which the surgical tool is currently located; and generate an acceleration projection along the predetermined tool path by computing a dot product of the tool path direction and the virtual acceleration vector.

13. The robotic surgical system of claim 10, wherein the control system is configured to:

define virtual tool path constraints configured to limit movement of the surgical tool to be along the predetermined tool path; and evaluate the effect of the virtual acceleration vector on the automated advancement of the surgical tool by being configured to simulate dynamics of the surgical tool in a virtual simulation based on the virtual tool path constraints, the predetermined feed rate and the virtual acceleration vector.

14. The robotic surgical system of claim 1, wherein the control system is configured to command the manipulator to initiate the automated advancement in response to the force/torque sensor receiving the input from forces/torques manually applied to the surgical tool by the user.

15. A computer-implemented method of operating a robotic surgical system, the robotic surgical system comprising a surgical tool, a manipulator configured to support the surgical tool, the manipulator comprising a plurality of links and joints, a force/torque sensor configured to measure forces/torques applied to the surgical tool by a user, and a control system, the computer-implemented method comprising the control system performing the following steps:

obtaining a predetermined tool path for the surgical tool, the predetermined tool path comprising an end location;

commanding the manipulator to perform an automated advancement of the surgical tool along the predetermined tool path in a first path direction and according to a predetermined feed rate to guide the surgical tool to the end location;

during the automated advancement of the surgical tool, receiving an input from the force/torque sensor in response to forces/torques applied to the surgical tool by the user;

evaluating an effect of the input from the force/torque sensor on the automated advancement of the surgical tool along the predetermined tool path in the first path direction and according to the predetermined feed rate;

based on evaluation of the effect, determining an effective feed rate and an effective path direction for the surgical tool with respect to the predetermined tool path; and determining a commanded action for the manipulator and the surgical tool with respect to the predetermined tool path based on the effective feed rate and effective path direction.

16. The computer-implemented method of claim 15, wherein the effective feed rate is greater than the predetermined feed rate and the effective path direction is the first path direction, and comprising the control system:

determining the commanded action to be automated advancement of the surgical tool along the predetermined tool path in the first path direction and according to the effective feed rate.

17. The computer-implemented method of claim 16, wherein automated advancement of the surgical tool according to the effective feed rate is based on a temporary input from the force/torque sensor and the commanded action comprises continuing automated advancement of the surgical tool according to the effective feed rate absent input from the force/torque sensor.

18. The computer-implemented method of claim 15, wherein the effective feed rate is less than the predetermined feed rate and the effective path direction is the first path direction, and comprising the control system:

determining the commanded action to be automated advancement of the surgical tool along the predetermined tool path in the first path direction and according to the effective feed rate or the predetermined feed rate.

19. The computer-implemented method of claim 15, wherein the effective path direction is a second path direction being opposite the first path direction, and comprising the control system:

determining the commanded action to be advancement of the surgical tool along the predetermined tool path in the second path direction and according to the effective feed rate.

20. The computer-implemented method of claim 19, further comprising simultaneously resisting advancement of the surgical tool in the second path direction by attempted automated advancement of the surgical tool in the first path direction.

21. The computer-implemented method of claim 15, comprising the control system:

detecting absence of the input from the force/torque sensor; and in response, commanding the manipulator to initiate or restore the automated advancement of the surgical tool along the predetermined tool path in the first path direction and according to the predetermined feed rate or according to a prior effective feed rate.

22. The computer-implemented method of claim 15, wherein the surgical tool is configured to be activated to remove tissue, and comprising the control system deactivating the surgical tool during the automated advancement of the surgical tool along the predetermined tool path.

23. The computer-implemented method of claim 15, comprising the control system:

determining, based on the input from the force/torque sensor, a virtual acceleration vector; and evaluating an effect of the virtual acceleration vector on the automated advancement of the surgical tool for determining the effective feed rate and the effective path direction for the surgical tool with respect to the predetermined tool path.

24. The computer-implemented method of claim 23, comprising the control system determining the virtual acceleration vector by:

modelling the surgical tool as a virtual rigid body comprising a virtual mass;

computing a force projection to the virtual rigid body based on the forces/torques applied to the surgical tool; and computing the virtual acceleration vector based on the force projection and the virtual mass.

25. The computer-implemented method of claim 24, comprising the control system determining the effective feed rate and the effective path direction for the surgical tool with respect to the predetermined tool path by:

computing a tool path direction based on a segment of the predetermined tool path on which the surgical tool is currently located; and generating an acceleration projection along the predetermined tool path by computing a dot product of the tool path direction and the virtual acceleration vector.

26. The computer-implemented method of claim 23, comprising the control system:

defining virtual tool path constraints for limiting movement of the surgical tool to be along the predetermined tool path; and evaluating the effect of the virtual acceleration vector on the automated advancement of the surgical tool by simulating dynamics of the surgical tool in a virtual simulation based on the virtual tool path constraints, the predetermined feed rate and the virtual acceleration vector.

27. The computer-implemented method of claim 15, comprising the control system commanding the manipulator to initiate the automated advancement in response to the force/torque sensor receiving the input from forces/torques manually applied to the surgical tool by the user.

\* \* \* \* \*